United States Patent
Goonetilleke et al.

(10) Patent No.: US 7,685,728 B2
(45) Date of Patent: Mar. 30, 2010

(54) METHOD AND APPARATUS FOR DETERMINING COMFORTABLE FOOTBED SHAPES

(75) Inventors: Ravindra Stephen Goonetilleke, Hong Kong (CN); Channa Patuwatha Witana, Hong Kong (CN)

(73) Assignee: The Hong Kong University of Science and Technology, Kowloon (HK)

( * ) Notice: Subject to any disclaimer, the term of this patent is extended or adjusted under 35 U.S.C. 154(b) by 172 days.

(21) Appl. No.: 12/057,563

(22) Filed: Mar. 28, 2008

(65) Prior Publication Data

US 2008/0276476 A1 Nov. 13, 2008

Related U.S. Application Data

(60) Provisional application No. 60/920,746, filed on Mar. 30, 2007.

(51) Int. Cl.
*A61B 5/103* (2006.01)

(52) U.S. Cl. .............................. 33/515; 33/512; 33/3 R; 600/592; 600/595

(58) Field of Classification Search .................. 33/515, 33/511, 512, 514.2, 2 R, 3 R, 6, 3 A, 3 B, 33/3 C
See application file for complete search history.

(56) References Cited

U.S. PATENT DOCUMENTS

| 2,043,187 | A | * | 6/1936 | Owens ........................ 600/592 |
| 4,802,494 | A | * | 2/1989 | Gardiner ........................ 33/3 C |
| 5,070,629 | A | | 12/1991 | Graham et al. |
| 5,282,328 | A | * | 2/1994 | Peterson ....................... 36/154 |
| 5,782,015 | A | | 7/1998 | Dananberg |
| 5,979,067 | A | * | 11/1999 | Waters ......................... 33/512 |
| 6,160,264 | A | | 12/2000 | Rebiere |
| 6,170,177 | B1 | * | 1/2001 | Frappier et al. ............... 33/515 |
| 6,219,929 | B1 | * | 4/2001 | Tasker et al. .................. 33/515 |
| 6,564,465 | B1 | * | 5/2003 | Ward ........................... 33/515 |
| 6,625,897 | B2 | | 9/2003 | Tadin |
| 6,845,568 | B2 | * | 1/2005 | Ward ........................... 33/515 |
| 6,860,034 | B2 | | 3/2005 | Schmid |
| 7,125,509 | B1 | * | 10/2006 | Smith .......................... 33/515 |
| 2005/0022407 | A1 | * | 2/2005 | Tadin .......................... 33/515 |
| 2006/0277772 | A1 | * | 12/2006 | Pupko .......................... 33/3 R |
| 2008/0028625 | A1 | * | 2/2008 | Nudelman et al. ............. 33/515 |
| 2009/0205213 | A1 | * | 8/2009 | Goonetilleke et al. .......... 33/3 R |

* cited by examiner

*Primary Examiner*—Yaritza Guadalupe-McCall
(74) *Attorney, Agent, or Firm*—Stites & Harbison PLLC; Ross F. Hunt, Jr.; Douglas E. Jackson

(57) ABSTRACT

A method and apparatus for determining the comfortable footbed shape for a person. The apparatus comprises a rear platform for supporting the rear of a foot, a front platform for supporting a forefoot, the height of at least one of said front and rear platforms being adjustable relative to the height of the other one of said platforms and fixable at a selected height relative to the other platform; and a supporting surface for accommodating the plantar surface of a foot, the supporting surface comprising a length of flexible material fixable mounted to and extending between said front and rear platforms. The apparatus can adjust the aforementioned components to various settings with a view to determining the plantar foot shape and the perceived comfort in any chosen posture.

20 Claims, 21 Drawing Sheets

METHOD AND APPARATUS FOR DETERMINING COMFORTABLE FOOTBED SHAPES

CROSS-REFERENCE TO RELATED APPLICATIONS

This application claims benefit of U.S. Provisional Application Ser. No. 60/920,746, filed Mar. 30, 2007.

FIELD OF THE INVENTION

The present invention relates to an apparatus that can be used for the determination and measurement of footbed shapes that are comfortable. It also relates to a system for obtaining the complete shape of a foot when placed on a simulated footbed. The shape or shapes obtained by the apparatus, correspond to different surfaces and can thereafter be used to make insoles or customized shoes that are comfortable to wear.

BACKGROUND OF THE INVENTION

Many methods or devices are used to obtain the plantar shape of the foot. These include molding the foot shape on a malleable material, plaster casting, optical sensing, contact measurement with sensors and so on. When a force is applied on a malleable material with a person's foot, it will deform to the shape of the footprint, which can thereafter be used to make an insole or other custom footbed. This method gives the natural shape of the foot with little resistance from the material. In reality, the natural shape of the foot is of little use due to the non-uniform bone and soft tissue structures in the foot. In other words, the deformations will be different in the different parts of the foot and the neutral shape will not match the varying stiffnesses of the foot. Methods such as plaster casting too have the same weakness as they give only the neutral shape of the foot. Optical sensing and contact sensor methods, even though very accurate, have their own weaknesses. They are ideal for obtaining the neutral shape of the foot but cannot be used to determine the shape inside a shoe or even in situations that simulate a shoe wherein the support surface should have the same parameters corresponding to a shoe.

Transparent material has been used to obtain the plantar shape of the foot but none of the previous methods are able to simulate all the footwear parameters together in order to determine the shape that is comfortable for the foot. Furthermore, most shoes, especially high-heeled shoes, which have such shapes are not comfortable for a person wearing them. Even though many different methods have been employed to determine foot shape, there is no robust method that allows the shape that is comfortable to be determined giving due consideration to the lengths, angles, and cushioning properties of the footbed surface.

SUMMARY OF THE INVENTION

In view of the drawbacks of the prior art, it would be desirable to be able to determine and utilize the footbed shape that is comfortable for a person. It would also be desirable to measure and/or capture an image of the surfaces of a foot will have when it is actually inside a shoe, high-heeled or otherwise, and/or when walking, running, sitting or standing.

The foot is comprised of 26 bones and soft tissues and the optimal configuration for the foot when standing on a surface is really not the same as that of the foot with no load acting on it. The bones and soft tissue structures of the foot will deform in different ways and it would be desirable to be able to capture the foot shape considering the various characteristics of the foot. The present invention aims to provide an apparatus and method for determining and measuring the shape of the foot as well as the shapes that are comfortable with varying heel length, heel angle, heel height, toe angle, and midfoot support length.

A first aspect of the present invention provides an apparatus comprising;
  a rear platform for supporting the rear of a foot;
  a front platform for supporting a forefoot;
  wherein the height of at least one of said front and rear platforms is adjustable relative to the height of the other one of said platforms and fixable at a selected height relative to the other platform;
  and a supporting surface for accommodating the plantar surface of a foot, the supporting surface comprising a length of flexible material mounted to and extending between said front and rear platforms.

The height of at least one of, but optionally both, the front and rear platforms are adjustable. An angle of inclination of the front and/or rear platforms may also be adjustable. Furthermore a horizontal distance between the rear platform and a forefoot receiving portion of the front platform may be adjusted The adjustments to height, distance, and angle may be continuous or in discrete steps depending upon the design of the apparatus.

The apparatus may be used to obtain the comfortable footbed shape for a person using a device. By adjusting the heights, distance and angles mentioned above the apparatus can simulate any heel height, heel length, heel angle, toe angle and midfoot support length of a shoe. The adjustments can be made mechanically, pneumatically or with electrical actuators. Furthermore, the support surface may be substituted for one having a different shape or different stiffness or resilience characteristics.

The support surface is preferably made of spring steel and further material may be placed on the support surface to simulate the material of the sole of a shoe. This further material may be changed to obtain comfortable foot shapes for differing materials that have differing levels of cushioning. Cushioning may be quantified using a compression tester to find the ideal material in terms of stiffness, energy loss, flexural rigidity, resilience, deflection, reactive force and other measures.

The apparatus may have an adjustable middle foot supporting member arranged for contacting a portion of the supporting surface. The middle foot supporting member provides extra support for the foot when necessary and may prevent the support surface from buckling if its stiffness or flexural rigidity is not right. It also influences the curvature of the supporting surface and may be adjusted in order to change the curvature of the supporting surface. For example the height, lateral positioning and/or angle of the middle foot supporting member may be adjusted.

Various designs of apparatus are possible in order to provide the desired adjustment of heights and angles. For example, the front or rear platform may be rotatable about an axis and its angle of inclination may be varied by one or more adjustment members such as screws, electrical or pneumatic actuators which support the platform. The platform may be mounted on a hinge which is rotatable relative to an axle. The height of the platforms may, for example, be adjusted by a plurality of height adjustment blocks placeable one on top of the other to adjust the height or by a screw, height adjustable pole or support or actuator for supporting the platform. Other possibilities will be apparent to a person skilled in the art.

The rear platform may have a replaceable foot supporting portion, which can be replaced by one or more other foot supporting portions having different angles of inclination and lengths. The rear platform may be arranged to receive a heel unit or component of any shoe so that the material deformation of the inserted part can give the plantar shape corresponding to the heel deformation when standing.

The apparatus may be integrated with, or provided together with, a separate optical device or touch probe for scanning or digitizing a foot placed on the support surface of the apparatus. The scanning or digitizing is preferably three dimensional, but may be two dimensional. Likewise, the scanning or digitizing is preferably for the whole foot, but may be for just a part of the foot such as the plantar or dorsal surface.

As the apparatus has several replaceable parts, it may be provided as a kit of parts for assembling into the full apparatus. Accordingly, as second aspect of the present invention provides a kit of parts comprising a rear platform for supporting the rear of a foot;

a front platform for supporting a forefoot;

a mechanism for adjusting the height of at least one of said front and rear platforms relative to the other one of said platforms and fixing said front or rear platform at a selected height relative to the other platform;

and a supporting surface for accommodating the plantar surface of a foot, the supporting surface comprising a length of flexible material mountable at one end to the front platform and the other end to the rear platform.

The kit of parts may comprise a plurality of supporting surfaces, having different shapes or resilience or stiffness characteristics. At any one time a selected one of said supporting surfaces may be mounted on said front and rear platforms. Likewise, the kit of parts may have a plurality of replaceable heel units for mounting on said rear platform and a plurality of replaceable toe spring units for mounting on said front platform. The toe spring units may be triangular, parabolic, elliptical or have other shapes and/or angles.

The second aspect of the invention may have any of the features of the first aspect of the present invention.

Typically, the apparatus is used to first determine a comfortable foot shape. The heel height, heel angle etc of the comfortable shape are then recorded and the shape of the foot in the comfortable position captured by scanning, digitizing, casting or other methods. Alternatively the apparatus may be used to measure the shape a foot assumes when placed on the apparatus in a predetermined position, e.g. corresponding to the heel height and angle of a shoe ordered by a customer, or a shape which has previously been determined to be comfortable.

Accordingly a third aspect of the present invention provides a method of determining the comfortable plantar shape of a foot comprising the steps of:

a) placing the rear of a foot on a rear platform, the forefoot on a front platform and resting the middle of the foot on a supporting surface comprising a strip of material between the front and rear platforms b) adjusting the height and/or an angle of inclination of at least one of the front and rear platforms and c) determining when the foot is comfortable.

After step c) the foot shape may be captured, e.g. by casting or scanning or digitizing with an optical device or mechanical probe.

Preferably the method uses an apparatus which has an adjustable middle foot supporting member positioned between the front and rear foot platforms and in contact with the supporting surface, and the method includes adjusting the middle foot supporting member to adjust a curvature of the supporting surface.

A fourth aspect of the present invention provides a method of measuring the plantar surface which a foot will assume in a shoe, comprising the steps of:

a) Providing an apparatus having a rear platform for supporting the rear of foot, a front platform for supporting a fore foot and a supporting surface comprising a strip of flexible material extending between the front and rear platforms.

b) adjusting the height and/or angle of inclination of one or both of the front and rear platforms to a predetermined or comfortable setting;

and c) placing the rear of a foot on the rear platform, the forefoot on the front platform and resting the middle of the foot on the supporting surface;

d) capturing the shape of the plantar surface of the foot placed on the supporting surface.

The foot may be placed on the supporting surface before or after adjustment of the apparatus to the predetermined or comfortable setting. The shape is captured in the predetermined or comfortable setting.

A middle foot supporting member may be used to adjust a curvature of the supporting surface.

Step d) in the fourth aspects of the present invention is typically carried out by using a mechanical or optical probe or optical scanner. Alternatively, an impression cast of the foot may be made and information extracted from the cast by contact or non-contact methods, including scanning and digitizing. Step d) preferably includes not just the plantar surface of the foot, but also the dorsal surfaces of the foot.

Thus, the complete shape of the foot can be obtained after which the complete shoe can be manufactured to provide a customized fit. A fifth aspect of the present invention is a method of manufacturing customized shoes comprising obtaining information about the foot by using any of the first to fourth aspects of the present invention. A still further aspect of the present invention is a shoe manufactured according to the fifth aspect of the present invention.

The above methods may use an apparatus having any of the features listed under the first and second aspects of the present invention.

One advantage of the present invention is that the apparatus can simulate the support surface deformations during different activities such as running, walking or playing other sports. The deformations will be first measured under simulated loading conditions with a compression tester and then those deformations can be incorporated using the mechanisms in the said apparatus so that the comfort levels can be evaluated.

The stiffness of the supporting surface material can be changed across the width (laterally) using strips of material in the lengthwise direction so that pronation and supination can be controlled and evaluated. Furthermore, the stiffness of the medial and lateral parts of the apparatus can be controlled to obtain similar deformation on the two sides of the foot to eliminate imbalance due to excessive pronation or supination.

The apparatus and methods of the present invention may also be used to design a custom insole for a shoe wherein the insole material will be deformed while standing on a comfortable supporting surface shape in a desired fashion, depending on the foam or material stiffness of the insole material. The material is placed on the supporting surface of the apparatus and tested in the appropriate simulated configuration of the shoe.

The required (or ideal or optimal) pressure patterns on the plantar surface of foot may be obtained by varying the shape and stiffness of the material so that a comfortable supporting surface can be generated. The pressure patterns may be obtained using pressure sensors between the foot and the said supporting surface wherein the electrical signals from the sensors are calibrated and displayed as pressure values on a display. The sensors are preferably thin, e.g. paper thin, such that they do not interfere or alter the shape of the foot or the supporting surface. When the shape of the supporting surface is changed, the pressure patterns will change as well. The ideal shape for the required pressure pattern can then be quickly determined using the said apparatus.

BRIEF DESCRIPTION OF THE DRAWINGS

Embodiments of the present invention will now be described with reference to the drawings, which are by way of example only and not to be taken to limit the scope of the invention. The drawings.

DETAILED DESCRIPTION OF THE INVENTION

Figure 1:
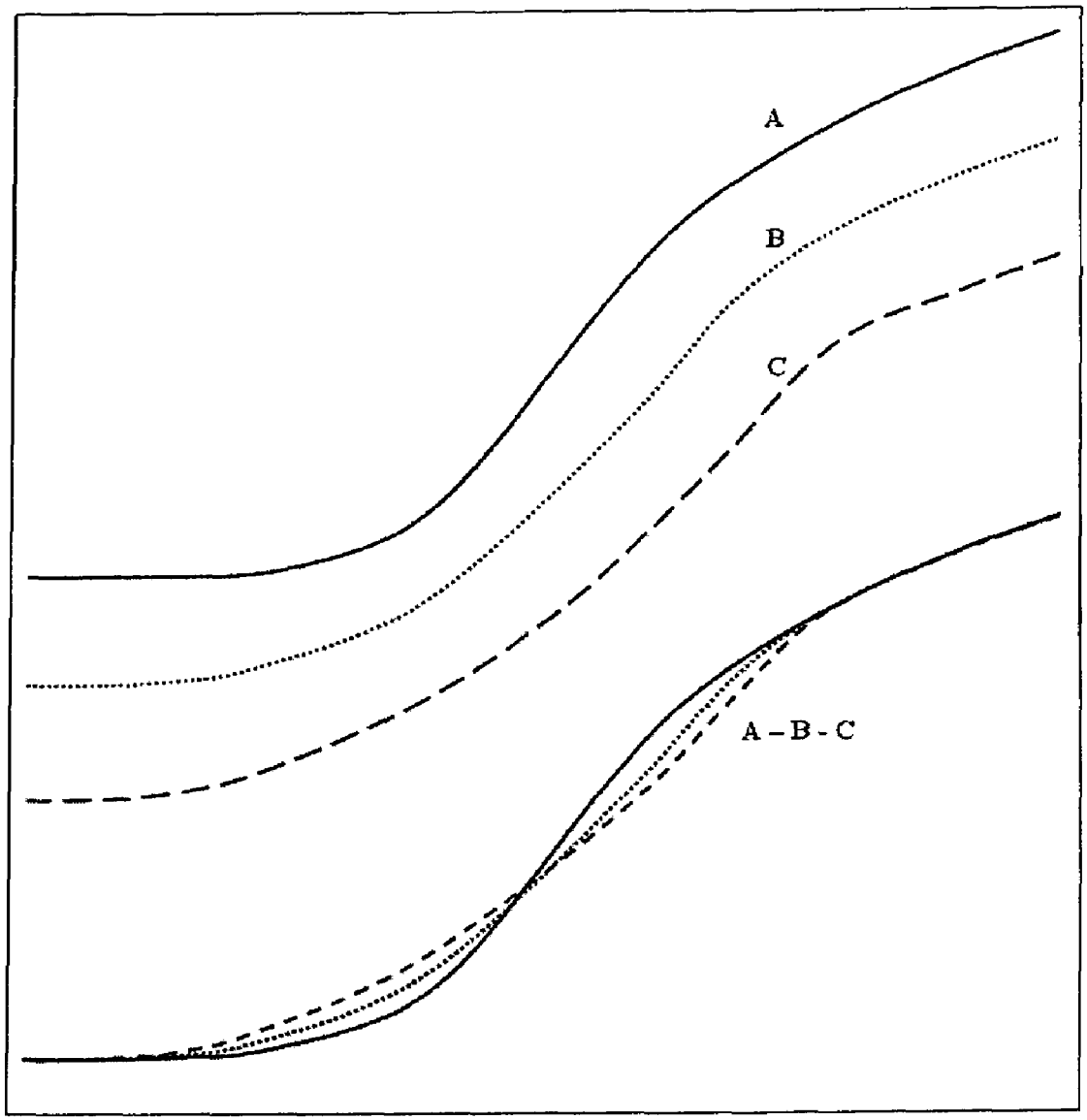
FIG. 1 illustrates sample shank curves used in shoes.

FIG. 1 illustrates examples of shank curves used in shoes.

Figure 2:
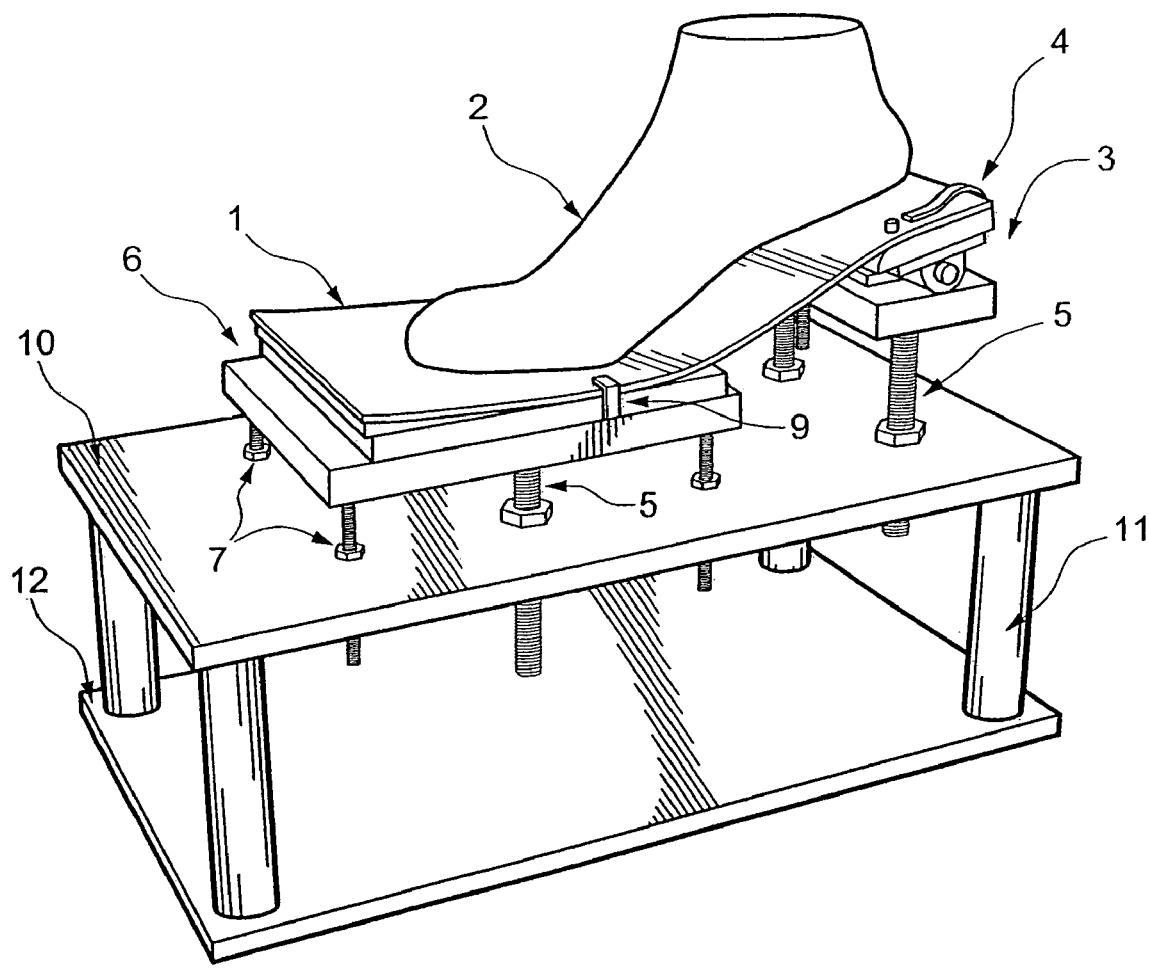
FIG. 2 is a side perspective view of an apparatus according to a first embodiment of the present invention.
Figure 3:
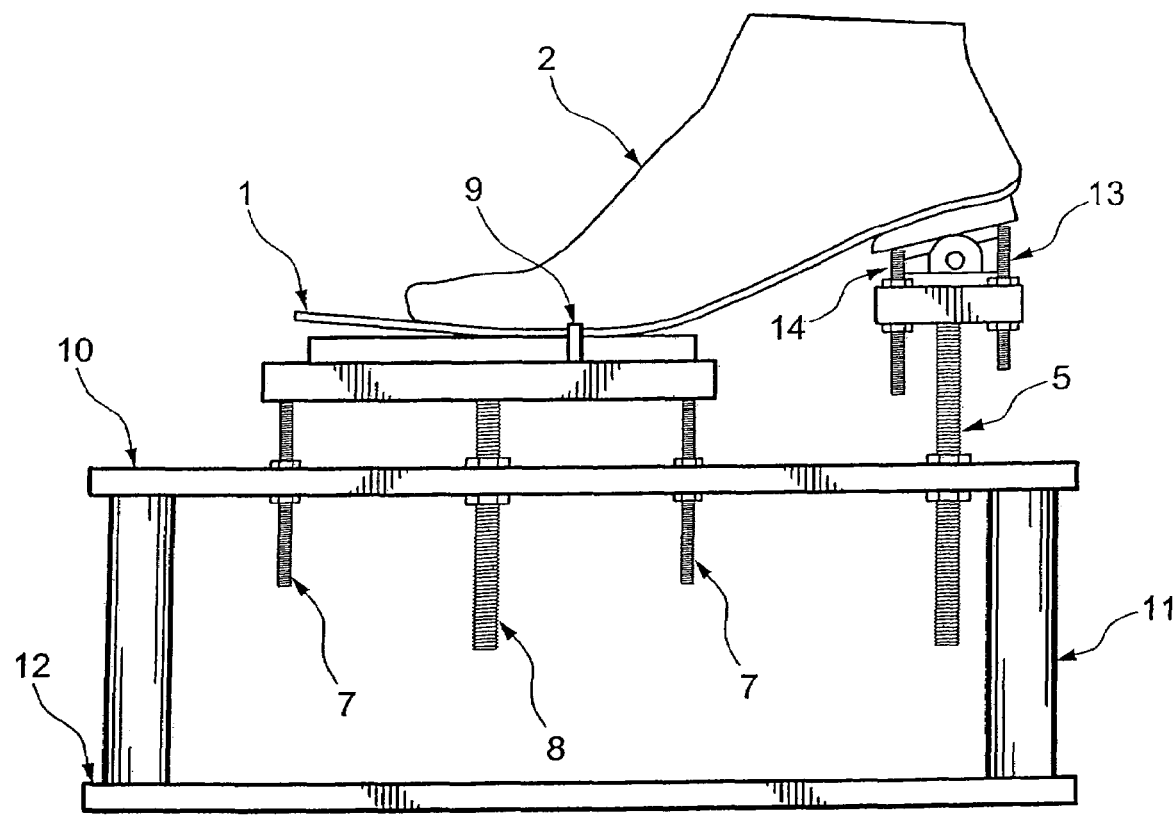
FIG. 3 is a side view of the apparatus of FIG. 2.

FIG. 2 and FIG. 3, illustrate a first embodiment of an apparatus for determining footbed shapes that are comfortable when worn. The apparatus comprises different surfaces on which a person can position their foot. It comprises a supporting surface 1, a rear platform 3 for supporting the rear of a foot, and a front platform 6 for supporting the front of a foot. The supporting surface 1 is mounted on the front and rear platforms and extends between them. In this embodiment one end of the supporting surface is rigidly fixed to the rear platform 3. The other end of the supporting surface 1 rests on the front platform 6. The middle portion of the supporting surface 1 is for the most part not supported underneath so that the compressive and tensile stresses generated internally due to the bending of the material will allow the shape to change.

The supporting surface 1 is preferably spring steel. However, any flexible material such as spring steel, polyurethane, or other thermoplastic or thermoset material having a flexural rigidity in the range of 0.03 to 1.0 $Nm^2$ can be used as the supporting surface.

When a person stands on the apparatus, their foot 2 will be resting on the supporting surface 1, where the plantar rearfoot and plantar forefoot regions of the person's foot 2 deform to the shape integrated in the rear platform 3 and the front platform 6. The plantar midfoot region of the foot 2 is accommodated and supported by the supporting surface 1 between the two platforms. The plantar midfoot region of the foot assumes a shape determined by the level of cushioning provided from the middle portion of the supporting surface 1, which is dependent on the supporting surface's material properties and its cross-sectional shape. Accordingly, by varying the type of material used for the supporting surface 1 and its cross-sectional shape, the plantar midfoot region of the foot 2 will subject to different levels of cushioning.

Figure 16:
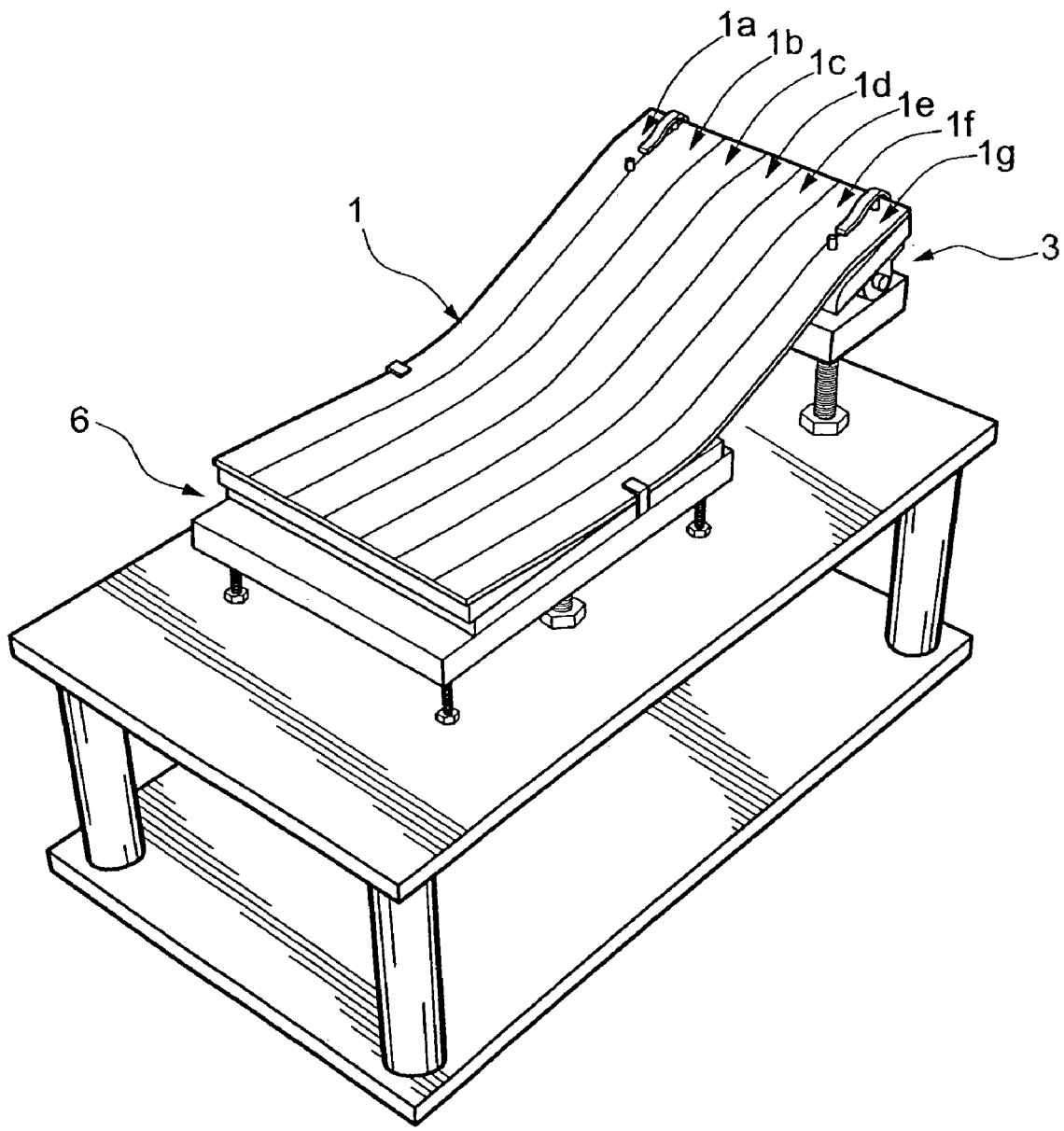
FIG. 16 is a perspective view of a supporting surface having a plurality of different portions having different characteristics.

In a preferred embodiment there are a plurality of different supporting surfaces having different shapes and different material properties. Any one of the supporting surfaces may be selected and mounted to the front and rear platforms of the apparatus. Thus, by selecting different support surfaces 1, different shoe types can be simulated. The supporting surface may be a uniform length of material or may comprises a plurality of portions having different properties, e.g. different stiffnesses and resilience properties. FIG. 16 shows a supporting surface comprising a plurality of lengthways strips 1a to 1g having different properties. In this way the properties of the supporting surface vary across its width. FIG. 16 is by way of example only, and the different portions may of course have different shapes. Furthermore an additional layer of material may be placed on the supporting surface 1 to simulate the cushioning material in the sole of a shoe. A plurality of thin pressure sensors may be placed between the foot and the supporting surface 1 in order to obtain a pressure profile for the sole of a shoe.

The rear platorm base 3 and front platform 6 can be adjusted to change their relative heights. In FIG. 3 this is by way of supports 7, 8 and 5 which are height-adjustable. It is preferred that both the front and rear platforms are height adjustable, however it would be possible for just one of the platforms to be height adjustable as this would still enable the relative height of the two platforms to be adjusted. The front 3 and rear 6 platforms have upper surfaces for supporting the front and rear portions of a foot respectively. The angles of inclination of these surfaces (hereinafter the 'angle of inclination of the platform') can be adjusted as well. It would also be possible to design the apparatus so that either the front or back platform (or both) may be moved horizontally backwards and forwards in order to vary the horizontal distance between the two, e.g. to accommodate different foot lengths.

By selecting of different support surfaces and adjusting the relative heights, horizontal separation and/or angles of inclination of the platforms, the resultant shape of the supporting surface can be adjusted to simulates a plurality of combinations of heel heights, heel wedge angles, heel seat lengths, supported midfoot length, and toe spring.

The apparatus has a size suitable for receiving a foot. In one embodiment this is 400 mm in length and 180 mm in width, but a range sizes will be possible and apparent to a person skilled in the art. It is envisaged that in general the heel height (height difference between rear and front platforms) will be between 0 and 200 mm inclusive, but values outside this range would also be possible. Regarding the length of the seat on the rear platform for supporting the rear foot it is envisaged that lengths between 20 to 100 mm will be most suitable, although the present invention is not limited to this. Similarly the distance between the front and rear platforms is likely to be in the range 50 to 150 mm and the angles of inclination of the front and rear platforms within the range of −45 degrees to +45 degrees.

The relative height, horizontal separation and angle of inclination of each platform may be adjusted continuously or in discrete steps, depending upon the design of the apparatus. In the first embodiment of the present invention, e.g. as illustrated in FIGS. 2 to 8, the height of each platform and the angle of inclination of the rear platform are adjustable continuously. Particular implementations of a mechanism for adjustment will now be described with reference to FIGS. 4 to 8. These are by way of example only and should not be taken to limit the scope of the invention, as alternatives and variations will be readily apparent to a person skilled in the art.

Figure 4:
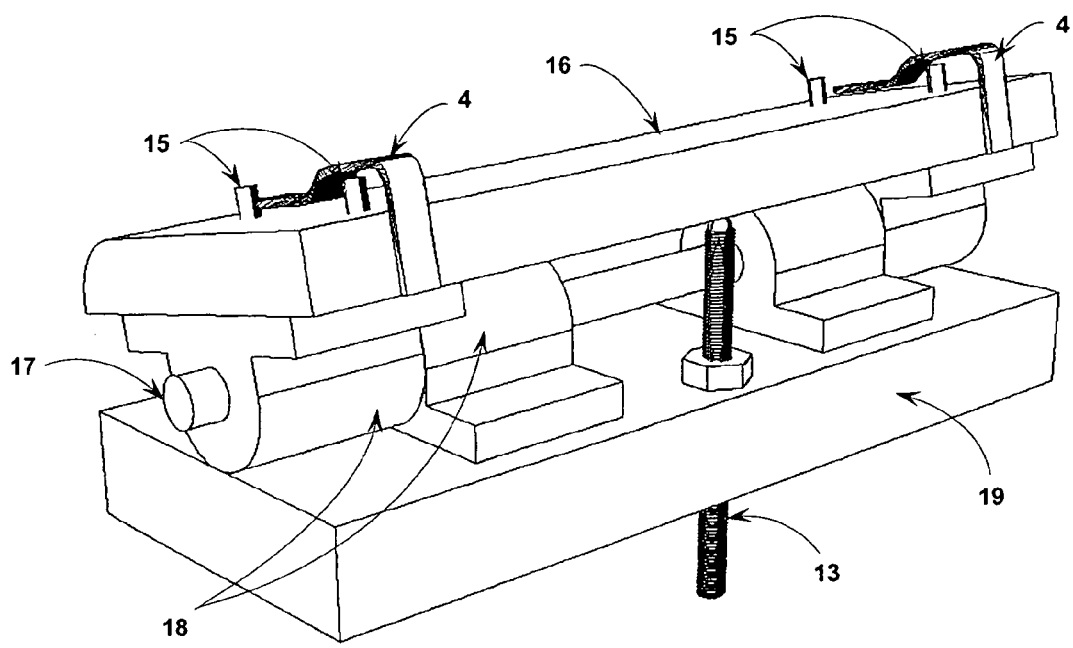
FIG. 4 is a rear perspective view of the rear platform angle varying mechanism.
Figure 5:
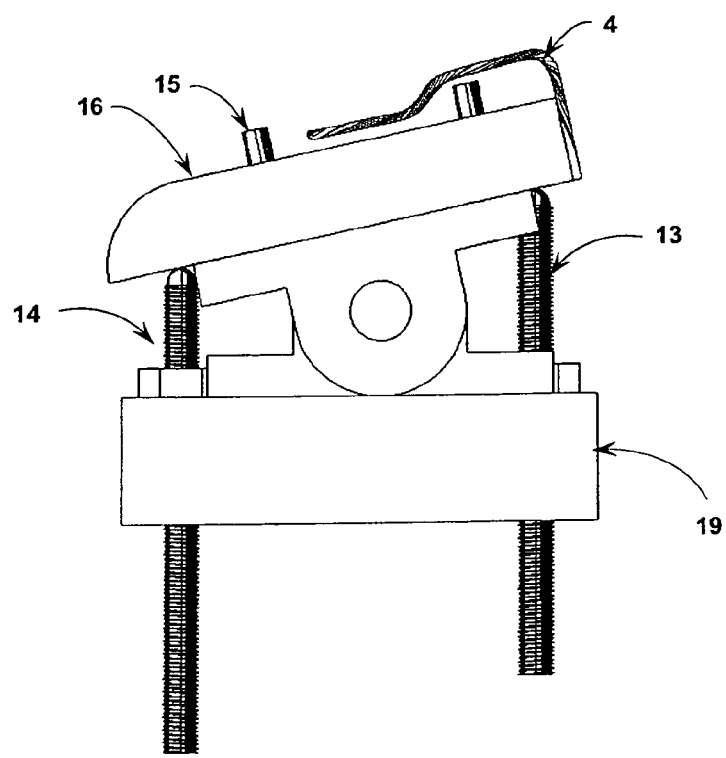
FIG. 5 is a side view of the rear platform angle varying mechanism.

FIG. 4 shows the tilting mechanism incorporated into the rear platform 3, which allows its angle of inclination to be adjusted. The top portion of the rear platform has a heel seat block 16. Four semi cylindrical blocks 18 and the shaft 17 comprise a hinge, to perform the tilting operation and, to locate the heel seat block 16 on to the rearfoot base bottom block 19. The two screws 13 & 14 may be adjusted to adjust the angle of inclination of the platform 3 (more precisely the angle of the upper heel block 16). The screws 13, 14 also help to fix the heel seat block 16 tightly after the required heel wedge angle is set as shown in FIG. 5. Other mechanism for adjusting the angle, such as nuts and bolts, height adjustable members, electrical and pneumatic actuators may be used instead of screws, and will be apparent to a person skilled in the art.

Figure 6:
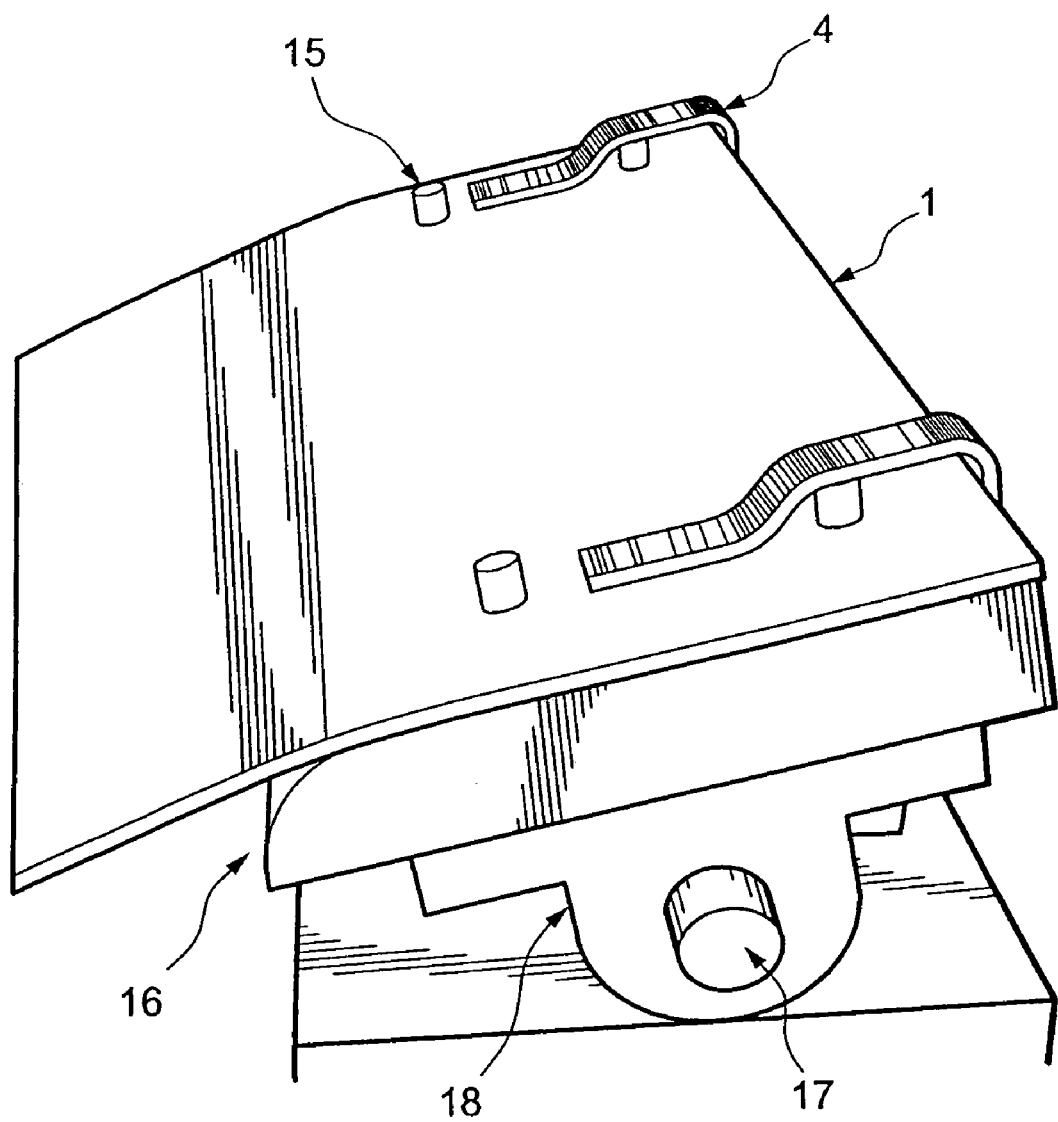
FIG. 6 is a side perspective view of a mechanism for fixing the supporting surface to the rear platform.

In this embodiment the support surface 1 is fixed to the rear platform base 3, but can be removed quickly so that the support surface 1 can be interchanged. There are four cylindrical pins 15 fixed on to the heel seat block 16 at predetermined distances (FIG. 6). The support surface 1 has four holes punched on it in order to match the locations of the four cylindrical pins 15, so that the support surface can be located on the rear platform 3 precisely and quickly. At the same time, two clamps 4 made out of spring steel are used to clamp the support surface 1 to the top surface of the heel seat block 16 as shown in FIG. 6. Other mechanisms for securing the support surface to the rear platform 3 are possible and will be apparent to a person skilled in the art.

Figure 7A:
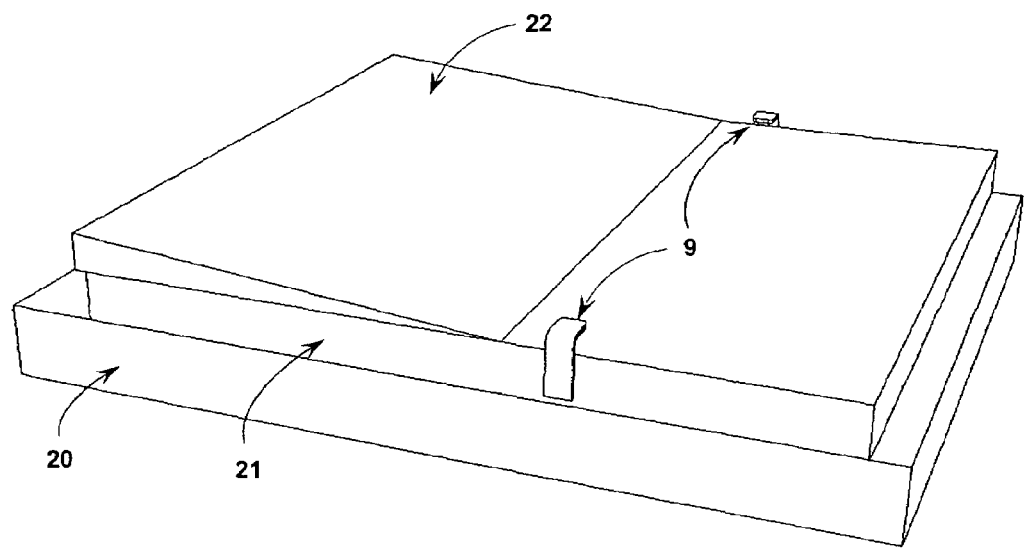
FIG. 7A is a side perspective view of the forefoot platform including a toe spring adjuster and supported midfoot length adjuster.
Figure 7B:
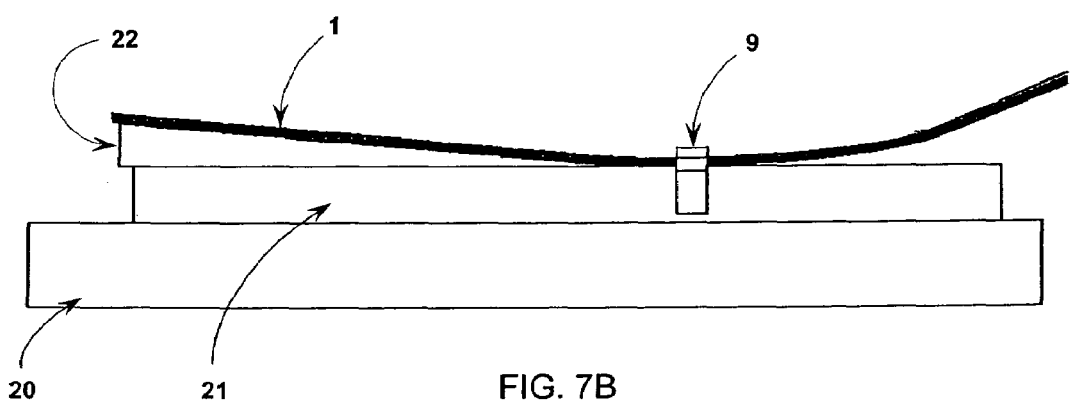
FIG. 7B is a side view of the forefoot platform.
Figure 8:
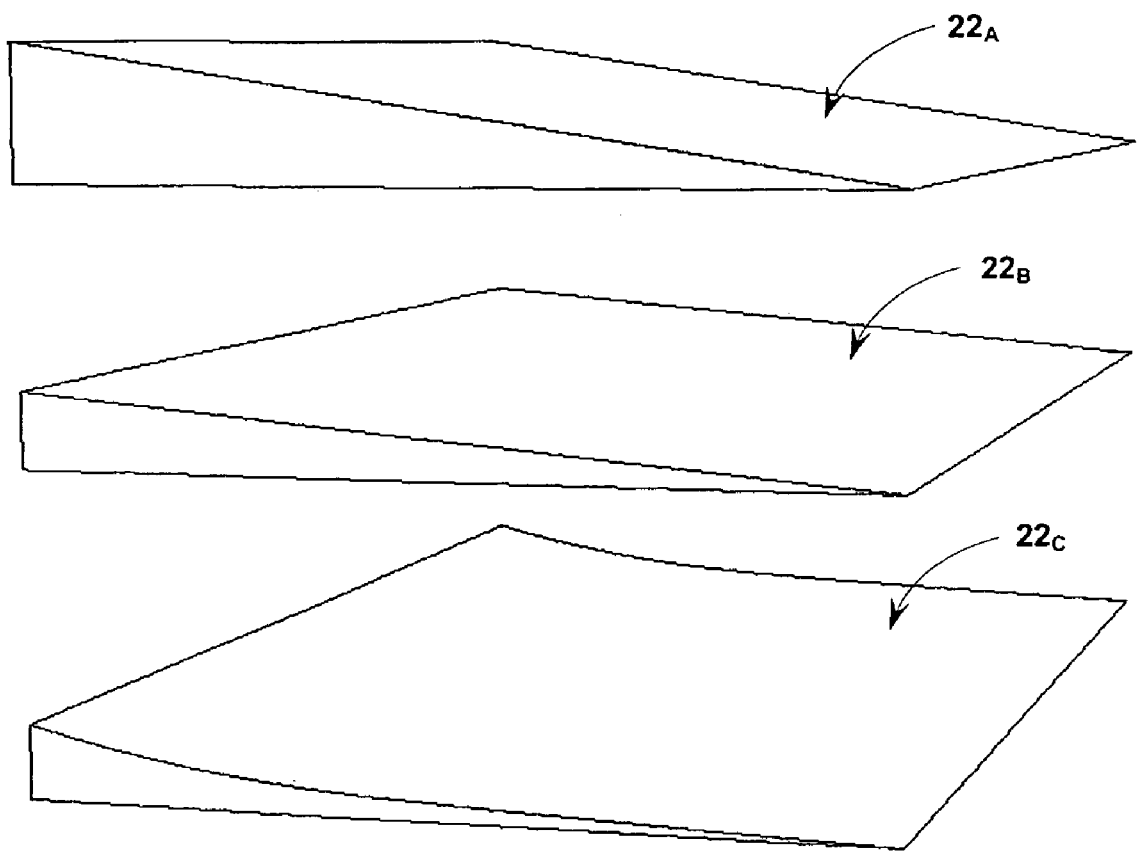
FIG. 8 illustrates alternative toe spring adjusters.

The front platform 6 comprises a toe spring wedge 22, front platform base bottom unit 20 and a sliding block 21 to mount toe spring wedge 22. As shown in FIG. 7B, the supporting surface 1 rests on the toe spring wedge 22 and the posterior part of the sliding block 21. Two guides 9 restrict the supporting surface from lifting off the sliding block 21 but allow the support surface 1 to slide through them. The sliding block 21 together with the two guides 9 can slide back and forth with respect to the front platform bottom piece 20, and the toe spring wedge 22 is capable of sliding back and forth on top of block 21, so that the support surface shape and the midfoot length can be adjusted to the requirements of a person's foot 2. The toe spring wedge 22 is designed to be interchangeable with other toe spring wedges that have different shapes and wedge angles. Therefore the apparatus will usually have a plurality of toe spring wedges, any one of which may be used at any one time. FIG. 8 shows three example toe spring wedges. The toe spring wedges 22A and 22B illustrate two different wedge angles and the toe spring wedge 22C shows another that would give a curvilinear profile for the toe region of the support surface 1.

In this embodiment, the heel height can be varied by changing the height of either the rear platform 3 or the front platform 6. The rear platform is mounted on to plate 10 using two mounting screws 5. The front platform is also mounted on to the same plate 10 using two mounting screws 8 and further supported by four guide screws 7. The height of each of the front and rear platforms may be adjusted by turning the screws. The arrangement described above is by way of example only and other mechanisms for adjusting the height of the platforms will be readily apparent to a person skilled in the art. For example, a nut and bolt arrangement, telescoping supports or pneumatic actuators could be used instead of screws. Plate 10 is supported over plate 12 by four cylindrical columns 11 as shown in FIG. 2 and FIG. 3.

In the first embodiment of the present invention, described above, the relative height of the front and rear platforms and the angle of inclination of the rear platform are adjustable continuously. The second embodiment of the present invention, which will now be described with reference to FIGS. 9 to 14, is the same, except that the height of the front platform and angle of inclination of the rear platform are adjustable in discrete steps. Examples of mechanisms for allowing discrete adjustment will now be described in more detail.

Figure 9:
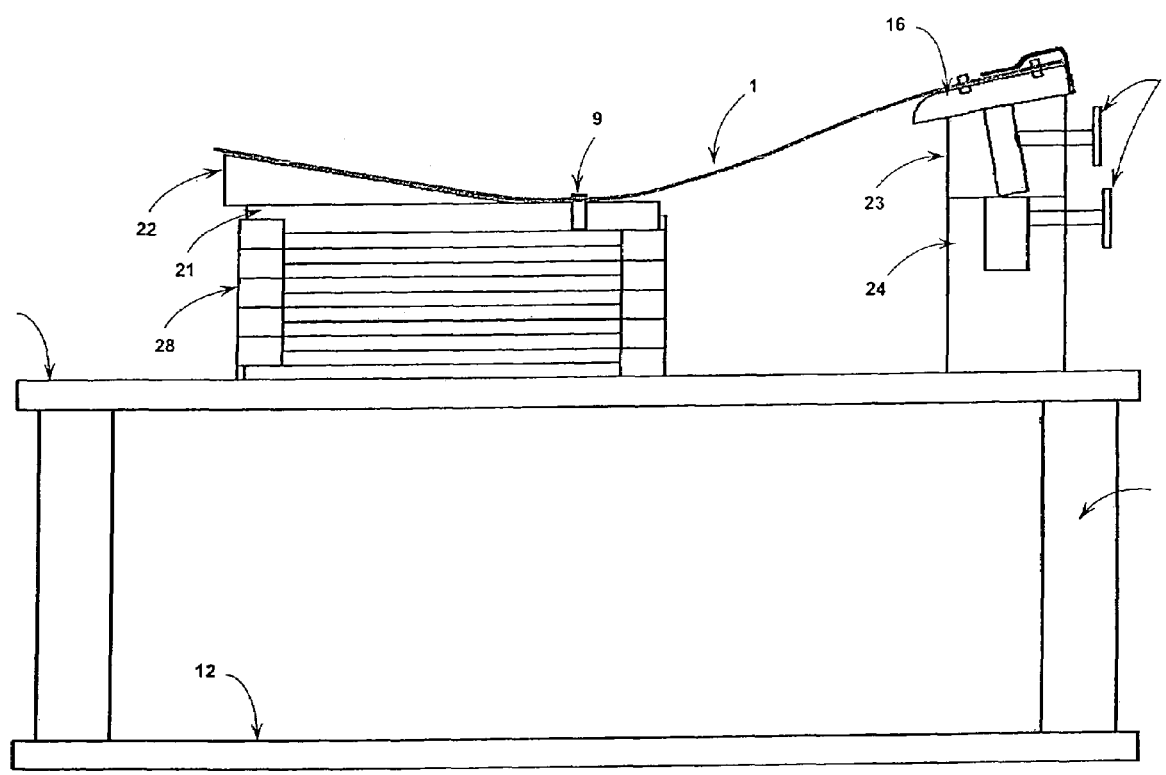
FIG. 9 illustrates an apparatus according to a second embodiment of the present; invention for determining the footbed shape at discrete levels of heel height, heel seat length, heel wedge angle, and toe spring angle.
Figure 10A:
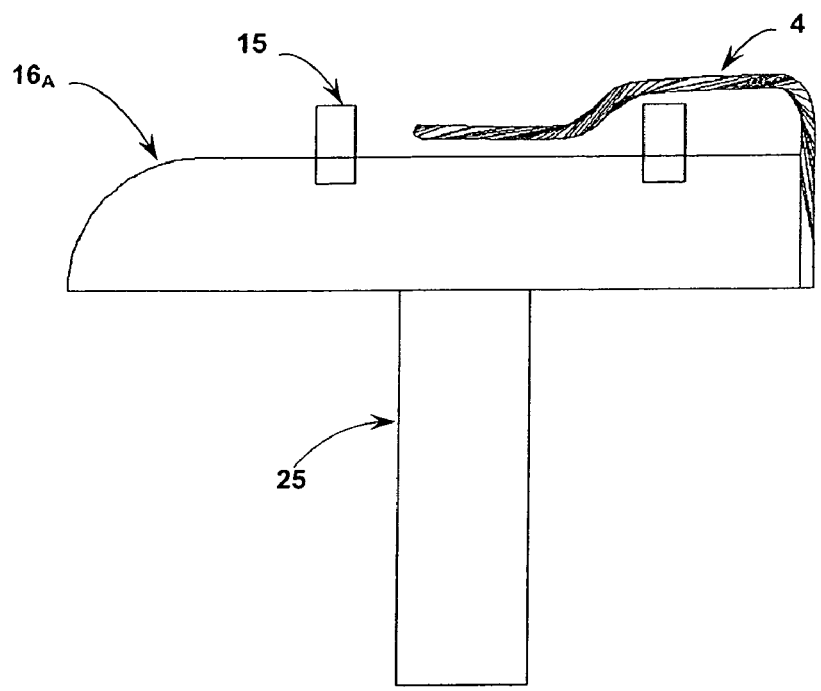
FIGS. 10A-10E illustrate alternative heel seat blocks for the rear platform, each having different angles of inclination.
Figure 10B:
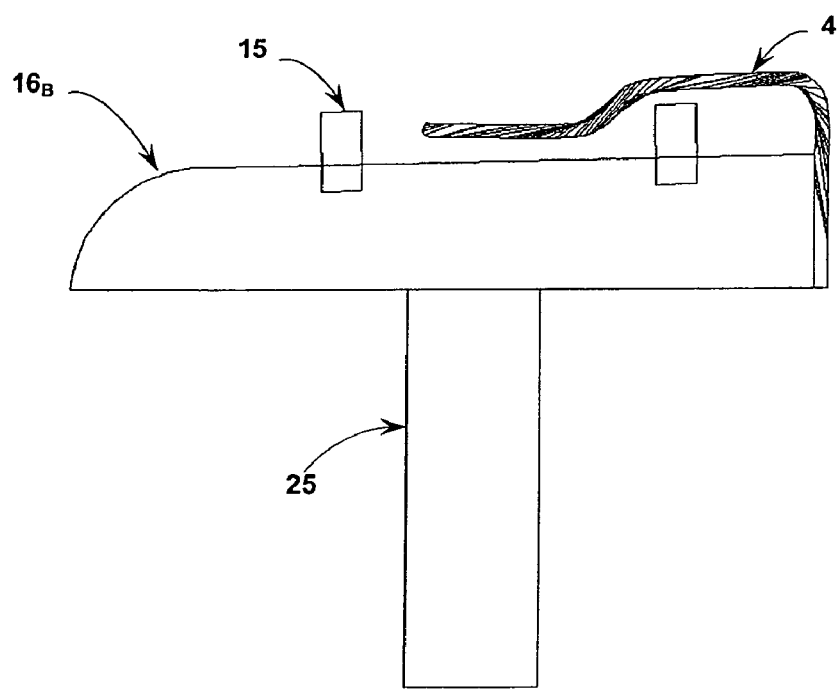
Figure 10C:
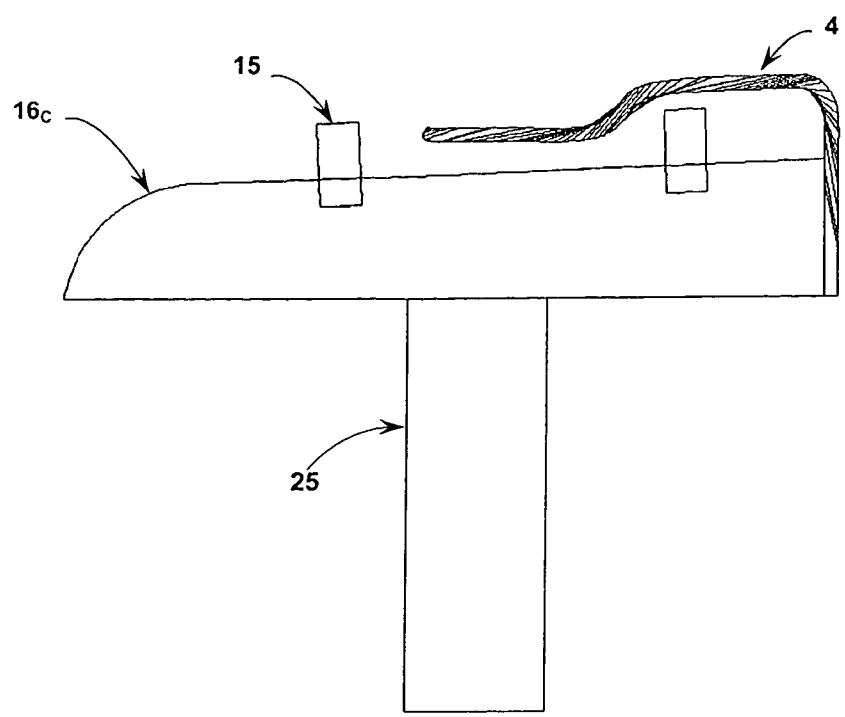
Figure 10D:
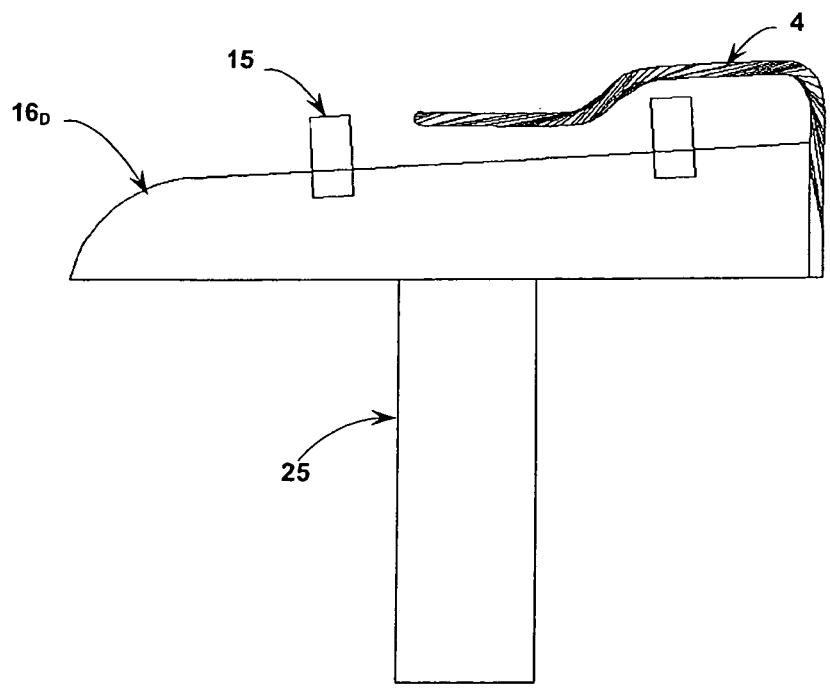
Figure 10E:
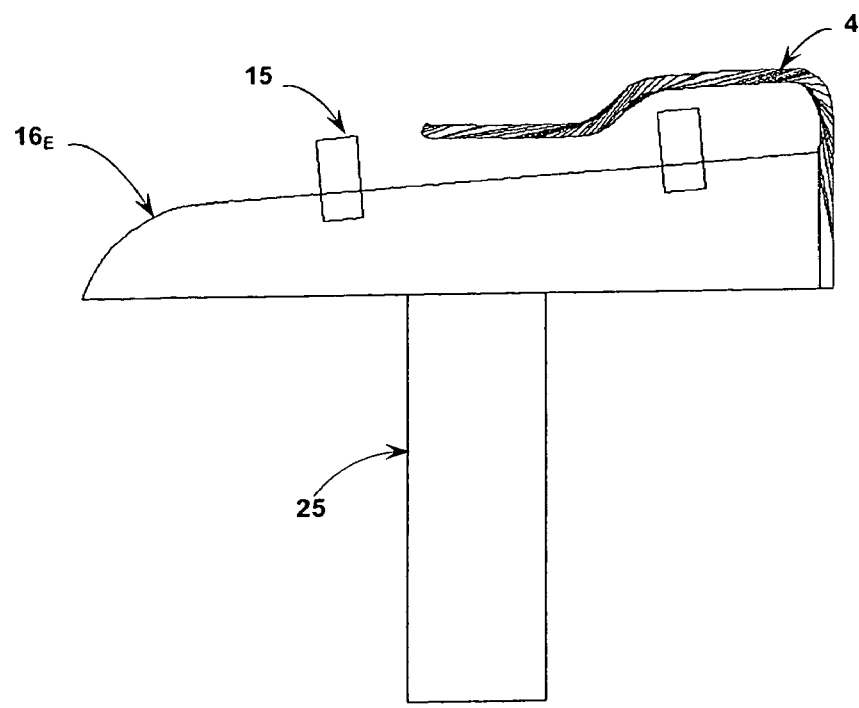
Figure 11:
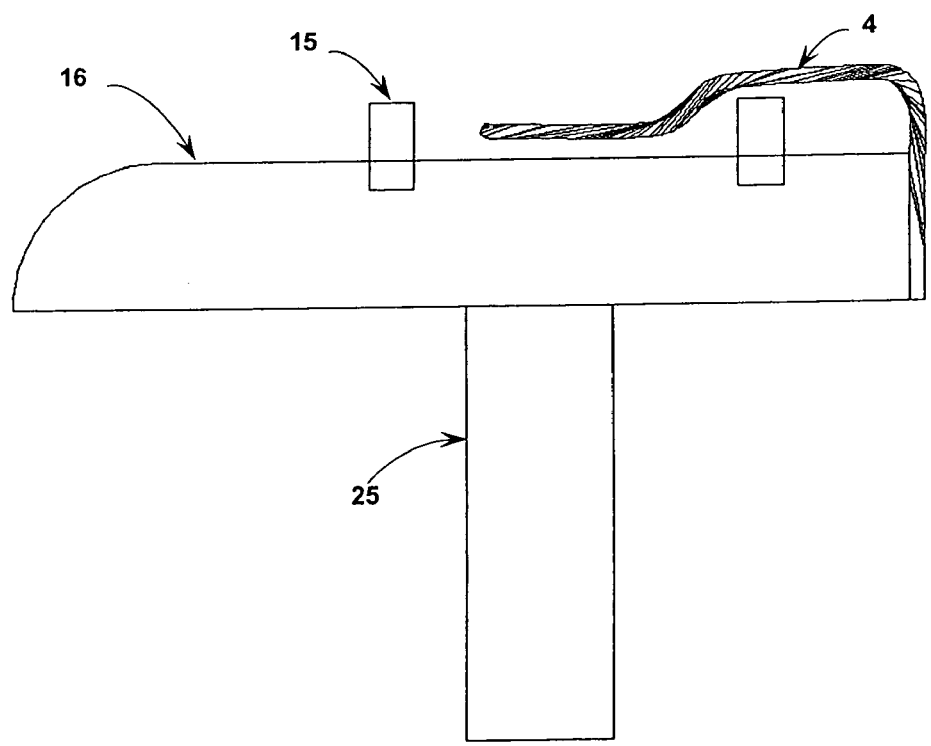
FIG. 11 is a side view of a heel seat block for the rear platform, which has 0 degree heel wedge angle and 50 mm heel seat length.
Figure 12A:
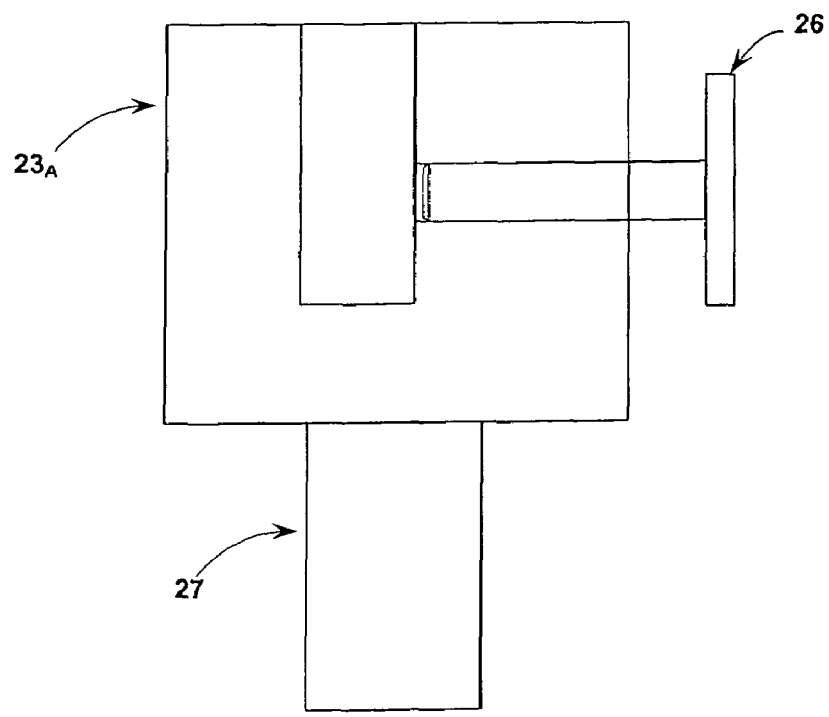
FIG. 12A-12G illustrate middle heel blocks for fixed heel wedge angles having a variety of angles.
Figure 12B:
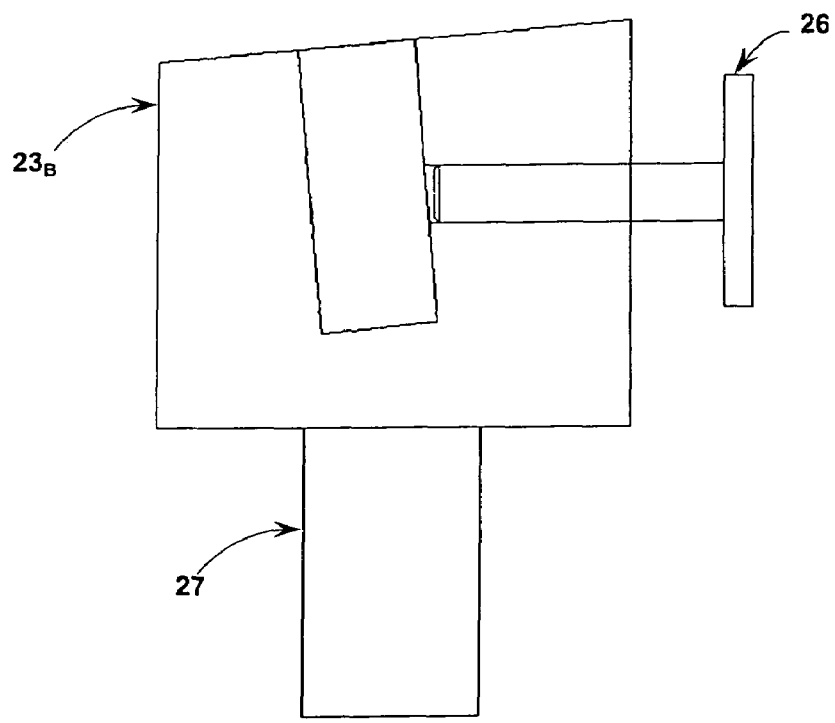
Figure 12C:
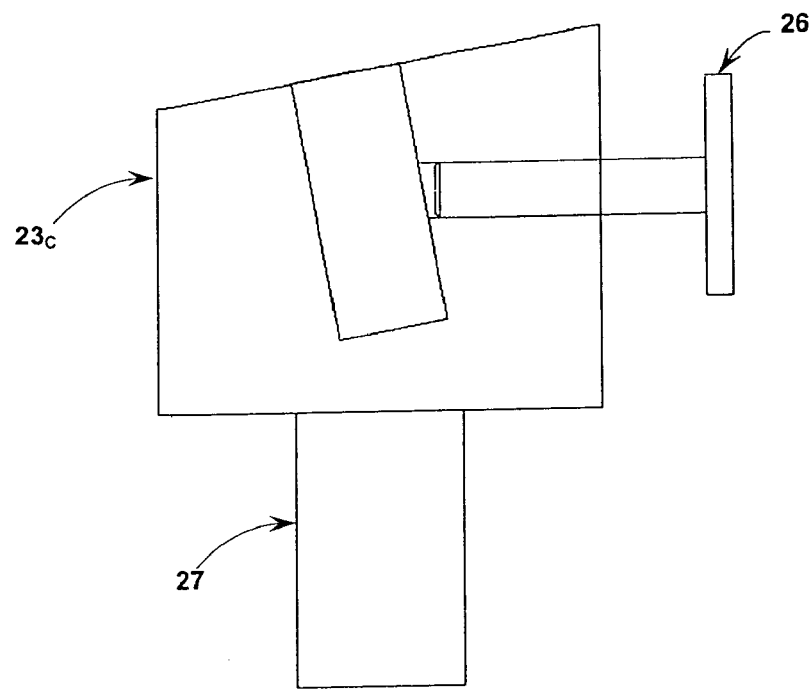
Figure 12D:
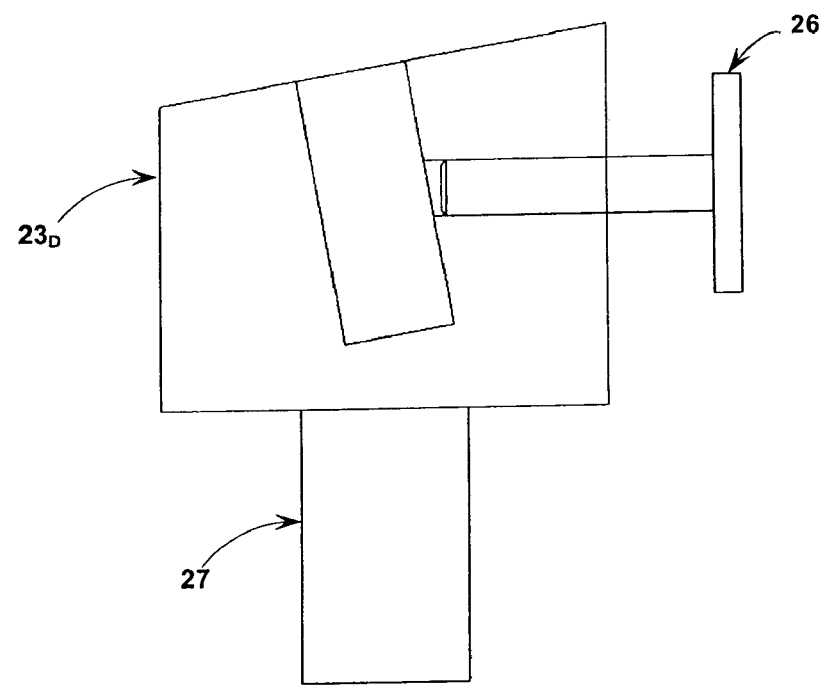
Figure 12E:
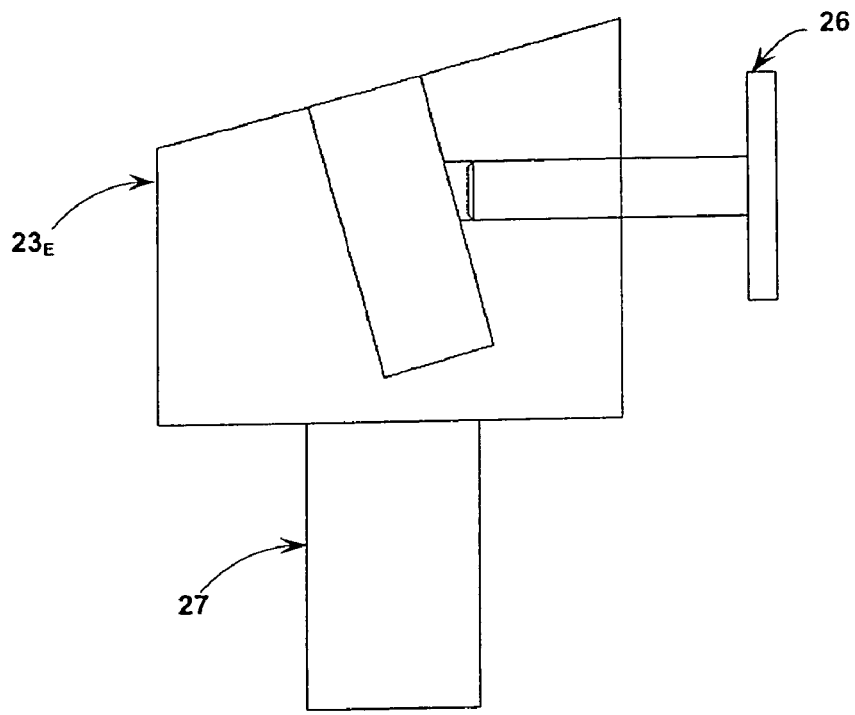
Figure 12F:
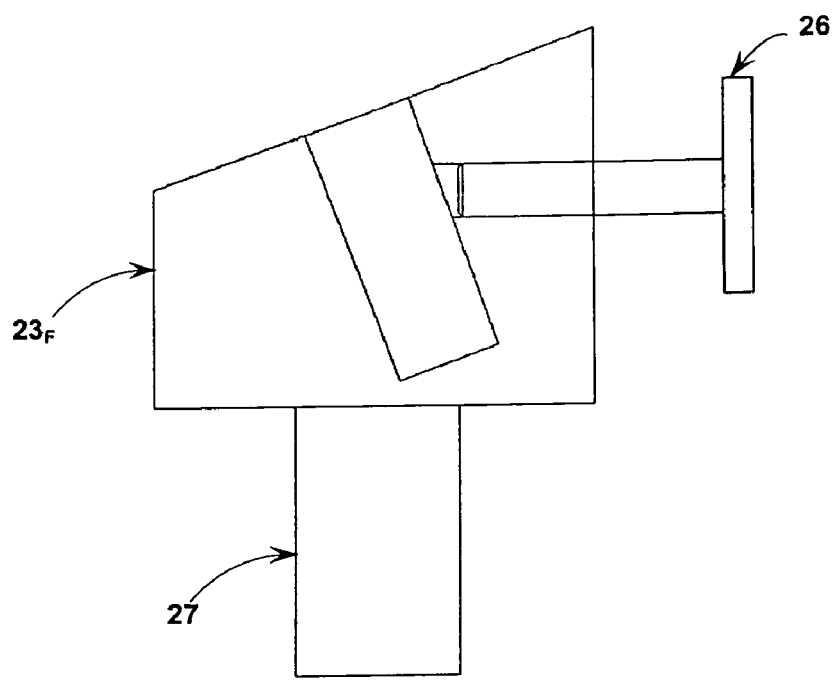
Figure 12G:
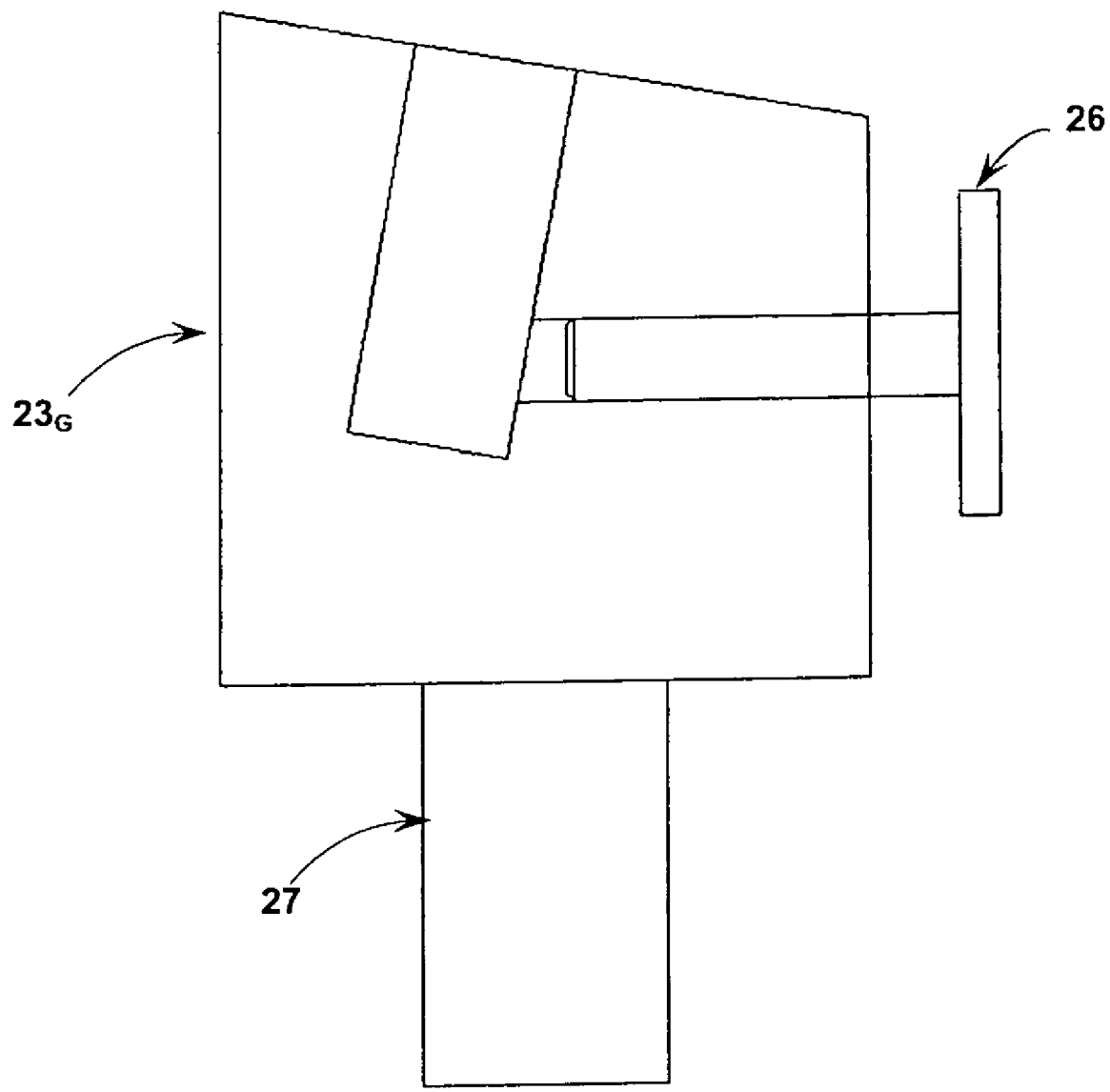
Figure 13:
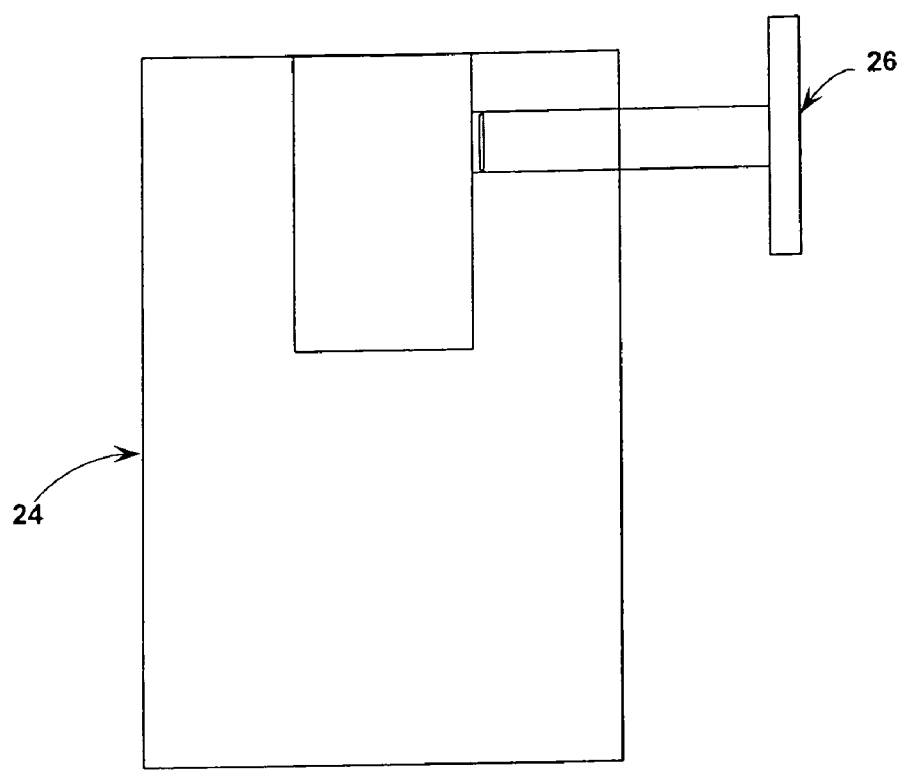
FIG. 13 illustrates a bottom heel block.
Figure 14:
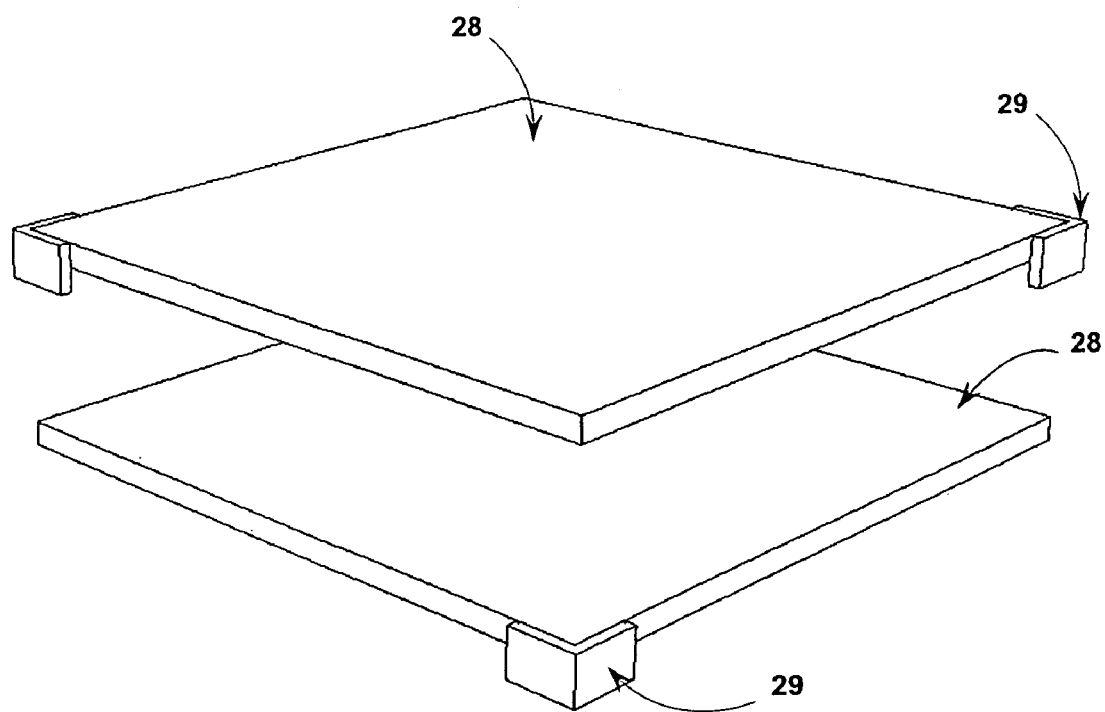
FIG. 14 is a perspective view of forefoot height adjustment blocks for the front platform.

The apparatus of FIG. 9 allows for measuring footbed shape at discrete levels of heel height, heel seat length, heel wedge angle, and toe spring angle. In this embodiment, the rear platform 3 comprises three main units, namely; heel seat base 16, middle heel block 23, and bottom heel block 24. FIG. 10A to FIG. 10E illustrate sample heel seat blocks $16_A$, $16_B$, $16_C$, $16_D$ & $16_E$ with heel wedge angles of 0, 1, 2, 3, and 4 degrees and 45 mm heel seat length respectively. Of course, the seat length of the block 16 can vary and need not be 45 mm. FIG. 11 illustrates a heel seat block 16 with a heel seat length of 50 mm, for example. There are two cylindrical guides 25 fixed to the bottom surface of heel seat block 16, so that the heel seat block 16 can be easily fixed to the middle heel block 23 with the use of its two mating guide holes and fastened with the screws having thumb wheels 26. FIG. 12A to FIG. 12G illustrate example middle heel blocks $23_A$, $23_B$, $23_C$, $23_D$, $23_E$, $23_F$ & $23_G$ with fixed heel wedge angles of 0, 5, 10, 15, 20, 25 and −5 degree respectively. By selecting an appropriate heel seat block 16 together with a middle heel block 23, the desired angle of inclination of the rear platform ('the heel wedge angle') can be achieved. The angle of inclination can be adjusted by swapping the heel seat block or middle heel block for a different one having a different angle.

In this way, a wide range of heel wedge angles can be achieved. There are two cylindrical guides 27 fixed underneath the middle heel block 23 which slide into mating holes provided in a top surface of the bottom heel block 24.

In this embodiment the height of the rear platform 3 is fixed, so the relative height is adjusted by adjusting the height of the front platform 6 only. Specifically, the heel height (relative height of the front and rear platforms) is adjusted by adding or removing front platform height adjustment blocks 28 as shown in FIG. 9. The adjustment is in discrete steps and the thickness of the front platform height adjustment block 28 determines the minimum adjustment of heel height. The front platform height adjustment block 28 has two corner guides 29 located diagonally, so that during stacking, adjustment block 28 can be rotated 90 degrees and fixed on top of the other with the help of two corner guides 29. The front platform 6 comprises the assembled height adjustment blocks 28, a sliding block 21 with two guides 9, and a toe spring wedge 22, which can slide back and forth on top of plate 10, so that shape of the supporting surface can be adjusted to the requirements of a person's foot 2.

A third embodiment will now be described with reference to FIG. 15. The third embodiment is the same as the first embodiment, but has a special mechanism 30 for adjusting the curvature of the supporting surface 1. In particular the mechanism 30 can support and adjust the shape of the midfoot section of the supporting surface 1 between the front and rear platforms. It also has the advantage of preventing the supporting surface 1 from buckling if the front and rear platforms and distance between them are not a perfect fit for the foot placed on the apparatus.

The mechanism 30 is a middle foot supporting member. It is positioned between the front and rear platforms 6, 3 and arranged to be capable of contacting the underside of the support surface so as to support it and influence its curvature. In this embodiment the middle foot support member 30 takes the form of a bar of approximately semi-cylindrical cross section and having a similar width to the front and rear platforms. The member 30 is hingedly attached to a support 31 so that its angle may be adjusted. The support 31 is height adjustable and may also be moved back and forward between the front and rear platforms. The shape of the middle part of the supporting surface 1 can be varied continuously by lifting, lowering or moving mechanism 30 back and forth on plate 10. This adjustment may be performed mechanically or using pneumatic or electrical actuators.

The middle foot support member for adjusting the curvature of the supporting surface may be added to first embodiment, second embodiment or any other implementations of the present invention.

Figure 17:
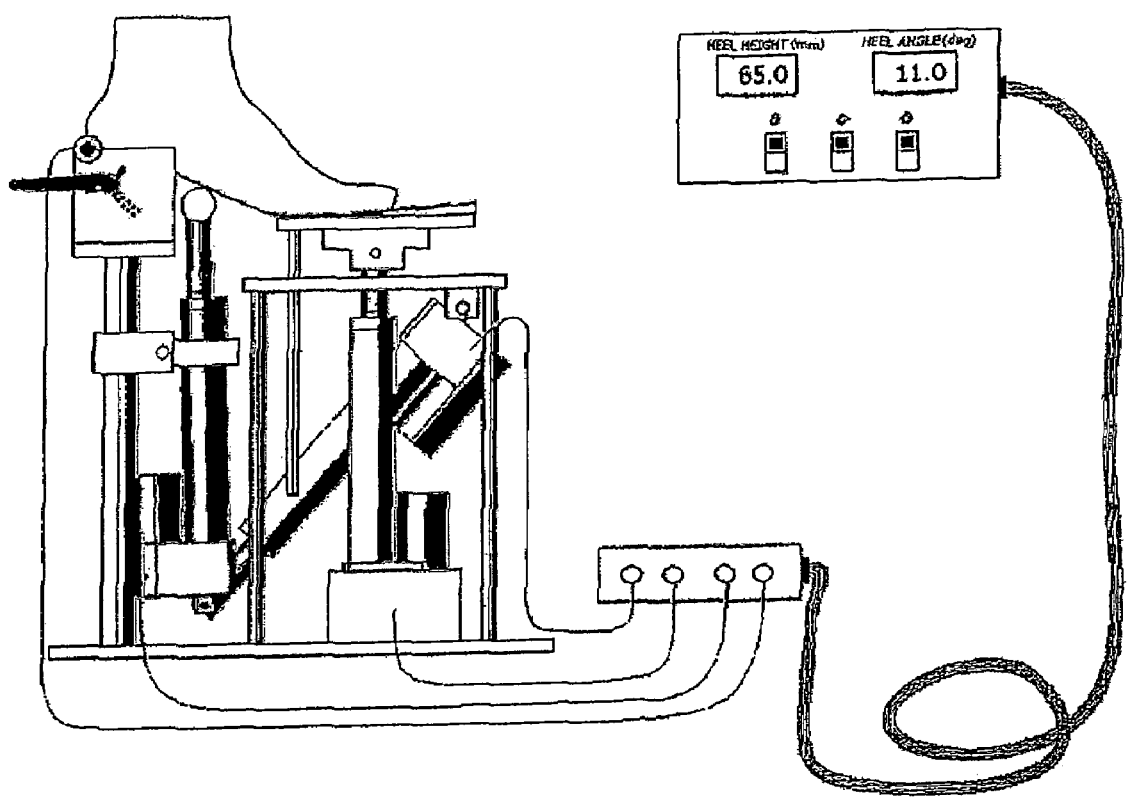
FIG. 17 is a functional side view of a fourth embodiment of the present invention which uses electrical or pneumatic actuators.

While the invention has been described above in mechanical form, e.g. with height adjusting screws and the like, it would be equally possibly for any of the various adjustments to be controlled and implemented by electrical actuators or pneumatic actuators. It would also be possible for the various heights and angles to be read by electrical devices, rather than mechanically. FIG. 17 illustrates an embodiment of the present invention in which the heights of the front platform, rear platform and middle foot supporting member, as well as the angle of inclination of the rear platform and middle foot supporting member are controlled by electrical actuators. The heel height (relative height of the rear platform relative to the front platform) and heel angle (angle of inclination of the rear platform) are read by electrical devices or control circuitry and displayed on a display device.

In use, a person puts their foot on the apparatus, so that the heel is on the rear platform and forefoot on the front platform. The supporting surface supports and changes shape to accommodate the plantar surface of the foot. The relative height of the front and rear platforms, angle of inclination of the rear platform, toe spring or angle of inclination on the front platform and distance between the front and rear platforms, and (if present the middle foot support member) are adjusted until a comfortable shape is found. The various parameters of the comfortable shape, in particular heel height and heel angle (i.e. relative height of platforms and angle of the rear platform) are recorded.

Two separate apparatus may be provided, one for the left foot and one for the right foot, so that a comfortable shape for both feet may be found at the same time. The person can move their feet to simulate walking or running, to check for comfort and so that the supporting surface changes shape to accommodate the actual shape of the foot during walking or running.

Once a comfortable fit has been found it is necessary to measure or capture the shape of the foot in this position. In particular the plantar surface of the foot, but it is highly desirable to capture the dorsal surface and sides also so that an image of the entire foot is captured and may be used in designing custom footwear.

There are three principle ways of measuring or capturing the shape of the foot. They are: digitizing, foot casting and foot scanning. While these methods are known in the art, it has previously only been possible to use them to capture the 'neutral' shape of the foot when flat on the ground. It has not been possible to capture the actual shape a foot assumes when wearing a shoe, or walking or running. Therefore the data captured from use of these methods in the prior art was incomplete and inaccurate, especially with regards to high heel shoes.

In the digitizing method a mechanical or optical probe is traced around the foot, when in a predetermined position on the apparatus according to the present invention. The predetermined position may be the comfortable position, determined as described above, or a position assumed by the foot when the apparatus has the heel height and heel angle according to a particular shoe design which the customer has ordered.

By tracing over the surface of the foot, the mechanical or optical probe measures and records (captures) the shape of the foot.

Figure 15:
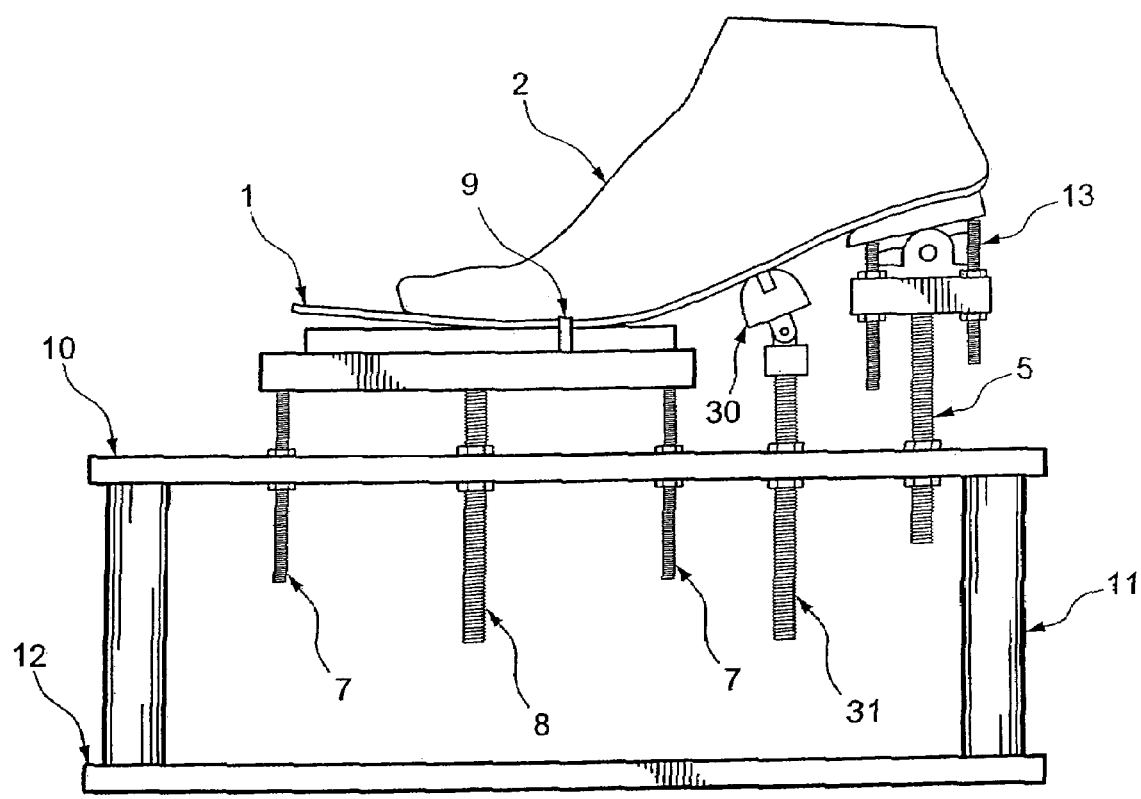
FIG. 15 is a side view of an apparatus according to a third embodiment of the present invention, having a middle foot support for adjusting the shape of the supporting surface extending between the front and rear platforms.

Alternatively, in order to capture the plantar surface of the foot, the probe may be moved along the supporting surface 1 in order to capture its two dimensional coordinates (e.g. in the plane shown in FIG. 15).

In the foot casting method the apparatus is surrounded by a surround casing, e.g. an acrylic box which is open at the top. The subject customer stands on the apparatus in the predetermined position and a mold mixture is then poured into the box. Molding materials used for making dentures, e.g. Jeltrate, or other suitable compositions may be used and will be apparent to a person skilled in the art. While the mold material is poured, the subject should remain still without any movement.

The subject may then take their foot out and let the mold dry for 3 to 4 minutes. To facilitate removal of the foot the box may have a removable heel side plate. This will make it easier to get the foot out from the solidified casting material without any cracks. The subject's foot will be taken out slowly and the heel plate will be put back on to the casting box.

A second material, which is capable of solidifying, e.g. Plaster of Paris, is then poured slowly into the box along the side walls. After pouring the Plaster of Paris mixture into the mold, a bolt may be inserted to the casting at the opening of the mold.

Finally, once the second material has solidified (e.g. after 30 minutes) the side plates of the box are removed and the solidified first material may be removed also. A casting model of the foot is now formed by the second material and may be allowed to dry (e.g. for 12 hours). Black color landmarks may be fixed on the foot casting by tracing its original landmark impressions (if needed) after it becomes dry.

In the scanning method, the apparatus is placed on a scanner bed. The subject stands on the apparatus in the predetermined position and their foot is scanned. The most suitable scanner will be apparent to a person skilled in the art. The scanner is an optical scanner and may take the form of an open-ended box into which the foot and apparatus according to the present invention are placed. Typically the scanner has one or more light sources (e.g. lasers) and one or more detectors in its walls. The foot is scanned by analyzing the detected reflected and/or transmitted laser beams. As scanners are known in the art, they need not be described further here.

The scanning device may be integrated with the apparatus according to the present invention, to provide a combined apparatus for determining and scanning a comfortable foot shape.

While the invention has been described above with reference to finding and measuring a comfortable foot shape, the same principles may be used to determine comfortable shapes for the back, neck and other body parts. For, example, an apparatus embodying similar principles could be used to find the comfortable shape for the back of a chair or sofa, pillow or mattress for a bed.

Figure 18:
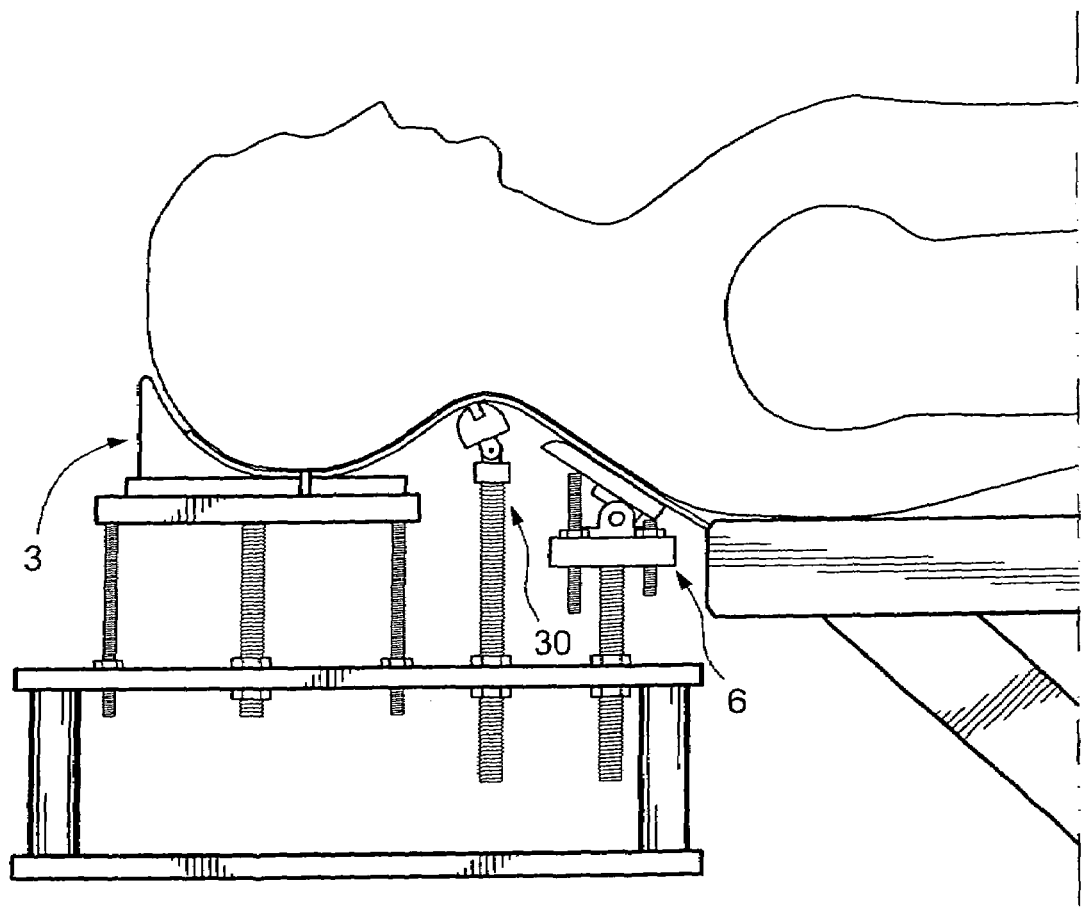
FIG. 18 is a side view of a fourth embodiment of the present invention for determining or measuring a comfortable neck shape.

FIG. 18 shows a fourth embodiment of the present invention, which is an apparatus for determining or measuring a comfortable shape for a neck. It comprises a first platform 3 for supporting the head, a second platform 6 for supporting the shoulders or lower portion of the neck, a middle support member 30 and a flexible supporting surface 1 mounted to and extending between the first and second platforms and middle support member.

In general functional terms, the parts are as described previously for the apparatus in the first to third embodiments of the present invention. The relative heights of the first and second platforms are adjustable, preferably by adjusting the height of either platform. The second platform 6 has an adjustable angle of inclination so that it may be adjusted to find a comfortable fit for supporting the neck. The middle support member 30 has an adjustable angle and height and may be moved backwards and forwards laterally between the first and second platforms such that it contacts the lower side of the supporting surface 1 and forms the supporting surface into a curve profile which fits the neck in a comfortable fashion.

Figure 19:
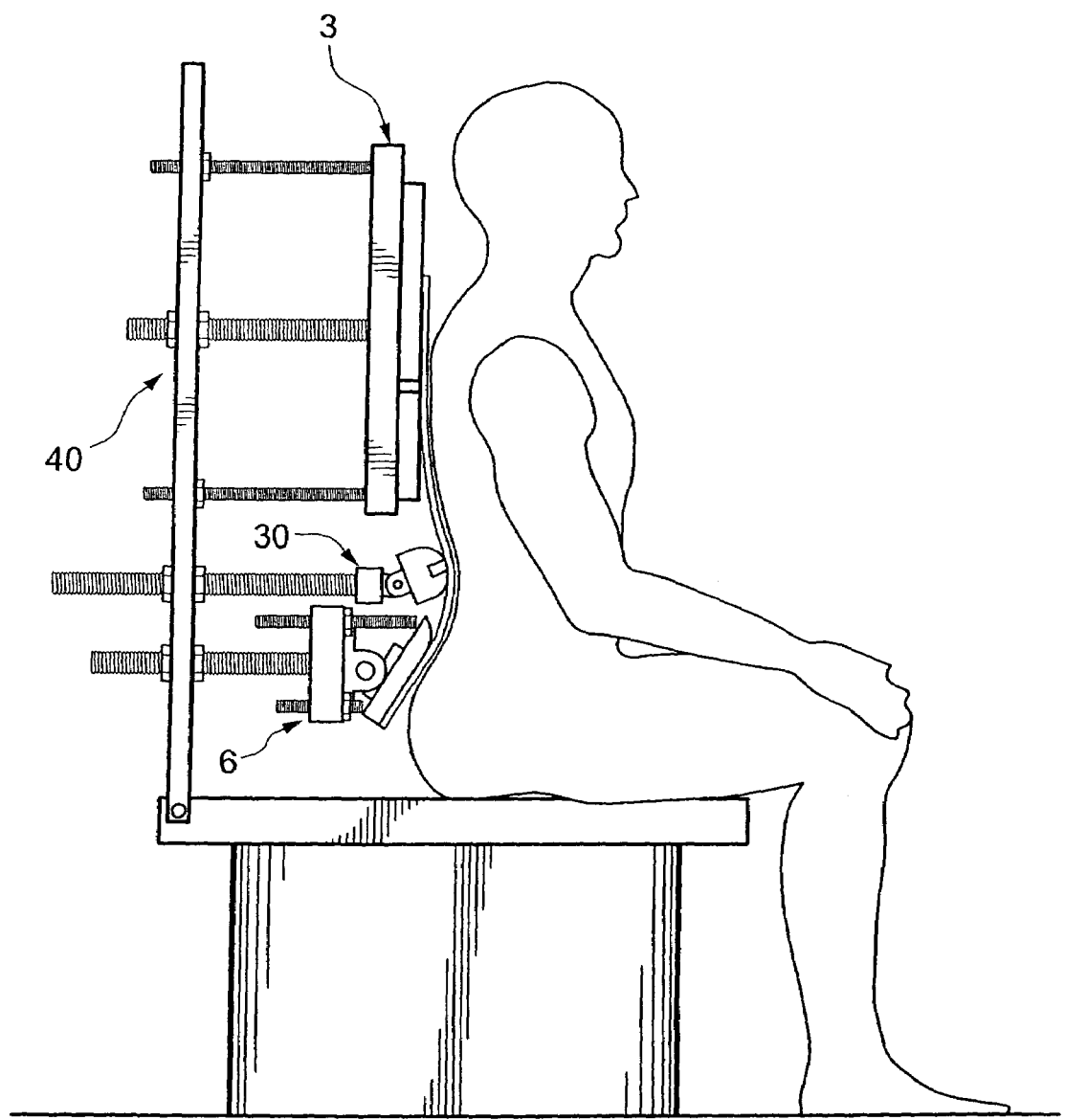
FIG. 19 is a side view of a fifth embodiment of the present invention for determining or measuring a comfortable back shape.

FIG. 19 illustrates a fifth embodiment of the present invention, which is an apparatus for determining and measuring the comfortable shape of a back and may be used to ergonomically design the back support of a chair or sofa. Its parts are similar to the parts in FIG. 18, except the first platform 3 supports the upper back, the second platform 6 supports the lower back and the middle supporting member supports the middle back. The platforms and middle supporting member are height adjustable, but in this context 'height' means the lateral distance from the back of the chair 40.

The invention has been described above with reference to certain particular embodiments, but the embodiments are by way of example only, and should not be taken to limit the spirit or scope of the invention which will includes all possible embodiments, modifications and variations falling within the scope of the appended claims.

The invention claimed is:

1. An apparatus comprising;
a rear platform for supporting the rear of a foot;
a front platform for supporting a forefoot;
the height of at least one of said front and rear platforms being adjustable relative to the height of the other one of said platforms and fixable at a selected height relative to the other platform;
and a supporting surface for accommodating the plantar surface of a foot, the supporting surface comprising a length of flexible material mounted to and extending between said front and rear platforms.

2. The apparatus of claim 1 further comprising an adjustable middle foot supporting member, said middle foot supporting member being arranged to contact a portion of the supporting surface.

3. The apparatus of claim 2 wherein the height of the middle foot supporting member is adjustable.

4. The apparatus of claim 2 wherein an angle of the middle foot supporting member is adjustable.

5. The apparatus of claim 2 wherein the lateral distance between the middle foot supporting member and the front or rear platform is adjustable.

6. The apparatus of claim 1 wherein an angle of inclination of the rear platform is adjustable.

7. The apparatus of claim 6 wherein the rear platform is rotatable about an axis and its angle of inclination may be varied by one or more adjustment members which support the platform.

8. The apparatus of claim 6 wherein the rear platform has a replaceable foot supporting portion, which can be replaced by one or more other foot supporting portions having different angles of inclination.

9. The apparatus of claim 1 wherein an angle of inclination of the front platform is adjustable.

10. The apparatus of claim 1 wherein the relative height of the front and rear platforms is adjustable continuously.

11. The apparatus of claim 1 wherein the relative height of the front and rear platforms is adjustable by one or more electrical actuators.

12. The apparatus of claim 1 having a plurality of replaceable supporting surfaces, each of which is mountable to the front and rear platforms and each of which has different characteristics.

13. The apparatus of claim 1 wherein the supporting surface is formed of a plurality of portions having different characteristics from each other; said characteristics being selected from the group comprising stiffnesses and resilience properties.

14. The apparatus of claim 1 further comprising an optical device or touch probe for obtaining a shape of a foot supported by the support surface.

15. A method of determining the comfortable plantar shape of a foot comprising the steps of:
a. placing the rear of a foot on a rear platform, the forefoot on a front platform and resting the middle of the foot on a supporting surface comprising a strip of material extending between and mounted to the front and rear platforms
b. adjusting the height and/or an angle of inclination of at least one of the front and rear platforms
c. determining when the foot is comfortable.

16. An apparatus for measuring the comfortable shape of a body part, comprising a first platform having a surface for supporting a first portion of the body part;

a second platform for supporting a second portion of the body part;

the height of at least one of said first and second platforms being adjustable relative to the height of the other one of said platforms and fixable at a selected height relative to the other platform;

and a supporting surface for accommodating the surface of the body part, the supporting surface comprising a length of flexible material extending between and mounted to said first and second platforms, and an adjustable middle supporting member for adjusting the curvature of the supporting surface.

17. The apparatus of claim 16 wherein the apparatus is designed for measuring the comfortable shape of a back or position of the spine, and wherein the first platform is arranged to support a portion of the upper back and the second platform is arranged to support a portion of the lower back, a person's posterior or base of the spine with an adjustable middle supporting member to adjust the curvature.

18. The apparatus of claim 16 wherein the apparatus is designed for measuring the comfortable shape of a neck, and wherein the first platform is arranged to support a person's head and the second platform is arranged to support a person's lower back or between the shoulders.

19. The apparatus of claim 16 wherein the middle supporting member is height adjustable.

20. The apparatus of claim 16 wherein the middle supporting member has an adjustable angle of inclination.

* * * * *